(12) United States Patent
Shoemaker et al.

(10) Patent No.: US 7,432,084 B2
(45) Date of Patent: Oct. 7, 2008

(54) METHODS FOR PREPARING NUCLEIC ACID SAMPLES

(75) Inventors: Daniel D. Shoemaker, San Diego, CA (US); Christopher D. Armour, Kirkland, WA (US); Philip W. Garrett-Engele, Seattle, WA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 330 days.

(21) Appl. No.: 10/485,008

(22) PCT Filed: Jul. 17, 2002

(86) PCT No.: PCT/US02/22787

§ 371 (c)(1),
(2), (4) Date: Aug. 19, 2004

(87) PCT Pub. No.: WO03/020979

PCT Pub. Date: Mar. 13, 2003

(65) Prior Publication Data

US 2005/0032057 A1 Feb. 10, 2005

Related U.S. Application Data

(60) Provisional application No. 60/316,648, filed on Aug. 31, 2001.

(51) Int. Cl.
*C12P 19/34* (2006.01)
(52) U.S. Cl. .................... 435/91.3; 435/91.21
(58) Field of Classification Search ............. 435/91.1, 435/91.2, 91.21, 6, 91.3
See application file for complete search history.

(56) References Cited

U.S. PATENT DOCUMENTS 5,409,818 A 4/1995 Davey et al.

(Continued)

FOREIGN PATENT DOCUMENTS

WO    WO 9708185    * 3/1997

(Continued)

OTHER PUBLICATIONS

Buck et al. Biotechniques, vol. 27, pp. 528-536, Sep. 1999.*

*Primary Examiner*—Kenneth R. Horlick
*Assistant Examiner*—Cynthia Wilder
(74) *Attorney, Agent, or Firm*—Christensen O'Connor Johnson Kindness PLLC

(57) ABSTRACT

In one aspect the present invention provides methods of synthesizing a preparation of nucleic acid molecules, the methods comprising the steps of: (a) utilizing an RNA template to enzymatically synthesize a first DNA molecule that is complementary to at least 50 contiguous bases of the RNA template; (b) utilizing the first DNA molecule as a template to enzymatically synthesize a second DNA molecule, thereby forming a double-stranded DNA molecule wherein the first DNA molecule is hybridized to the second DNA molecule; (c) utilizing the first or second DNA molecule of the double-stranded DNA molecule as a template to enzymatically synthesize a first RNA molecule that is complementary to either the first DNA molecule or to the second DNA molecule; and (d) utilizing the first RNA molecule as a template to enzymatically synthesize a third DNA molecule that is complementary to the first RNA molecule. In another aspect, the present invention provides processed DNA samples prepared by a method of the invention for synthesizing a preparation of nucleic acid molecules. In another aspect, the present invention provides methods for hybridizing a processed DNA sample to a population of immobilized nucleic acid molecules.

50 Claims, 2 Drawing Sheets

U.S. PATENT DOCUMENTS

| | | |
|---|---|---|
| 5,665,545 A | 9/1997 | Malek et al. |
| 5,914,229 A | 6/1999 | Loewy |
| 6,261,770 B1 | 7/2001 | Warthoe |
| 6,271,002 B1 | 8/2001 | Linsley et al. |
| 6,794,141 B2 * | 9/2004 | Erlander et al. ............ 435/6 |

FOREIGN PATENT DOCUMENTS

| | | | |
|---|---|---|---|
| WO | WO 9955378 | * | 4/1999 |

* cited by examiner

SEQUENCE LISTING

```
<160> NUMBER OF SEQ ID NOS: 7

<210> SEQ ID NO 1
<211> LENGTH: 12
<212> TYPE: DNA
<213> ORGANISM: Artificial Sequence
<220> FEATURE:
<223> OTHER INFORMATION: T7 RNA Polymerase Promoter

<400> SEQUENCE: 1
actataggga ga                                                          12

<210> SEQ ID NO 2
<211> LENGTH: 21
<212> TYPE: DNA
<213> ORGANISM: Artificial Sequence
<220> FEATURE:
<223> OTHER INFORMATION: First Primer Molecule ShT7N9
<220> FEATURE:
<221> NAME/KEY: misc_feature
<222> LOCATION: (1)..(21)
<223> OTHER INFORMATION: Wherein N=A, C, G, T or I

<400> SEQUENCE: 2
actataggga gannnnnnnn n                                                 21

<210> SEQ ID NO 3
<211> LENGTH: 21
<212> TYPE: DNA
<213> ORGANISM: Artificial Sequence
<220> FEATURE:
<223> OTHER INFORMATION: Primer ShDNP256
<220> FEATURE:
<221> NAME/KEY: misc_feature
<222> LOCATION: (1)..(21)
<223> OTHER INFORMATION: Wherein N=A,C,G,T or I

<400> SEQUENCE: 3
tagatgctgt tgnnnnnnnn n                                                 21

<210> SEQ ID NO 4
<211> LENGTH: 12
<212> TYPE: DNA
<213> ORGANISM: Artificial Sequence
<220> FEATURE:
<223> OTHER INFORMATION: Defined sequence portion of Primer ShDNP256

<400> SEQUENCE: 4
tagatgctgt tg                                                          12

<210> SEQ ID NO 5
<211> LENGTH: 26
<212> TYPE: DNA
<213> ORGANISM: Artificial Sequence
```

```
<220> FEATURE:
<223> OTHER INFORMATION: T7 Primer

<400> SEQUENCE: 5
aattaatacg actcactata gggaga                                          26

<210> SEQ ID NO 6
<211> LENGTH: 24
<212> TYPE: DNA
<213> ORGANISM: Artificial Sequence
<220> FEATURE:
<223> OTHER INFORMATION: DP256 Primer

<400> SEQUENCE: 6
gttcgagacc tctagatgct gttg                                            24

<210> SEQ ID NO 7
<211> LENGTH: 9
<212> TYPE: DNA
<213> ORGANISM: Artificial Sequence
<220> FEATURE:
<223> OTHER INFORMATION: Random Oligonucleotide
<220> FEATURE:
<221> NAME/KEY: misc_feature
<222> LOCATION: (1)..(9)
<223> OTHER INFORMATION: Wherein N=A,C,G,T or I

<400> SEQUENCE: 7 nnnnnnnnn                                                              9
```

METHODS FOR PREPARING NUCLEIC ACID SAMPLES

CROSS-REFERENCE TO RELATED APPLICATION

This application claims benefit of Provisional Application No. 60/316,648, filed Aug. 31, 2001.

FIELD OF THE INVENTION

The present invention relates to methods for preparing nucleic acid samples that are useful for screening populations of immobilized nucleic acid molecules, such as DNA molecules immobilized on a DNA microchip.

BACKGROUND OF THE INVENTION

The characterization of cellular gene expression finds application in a variety of disciplines, such as in the analysis of differential expression between different tissue types, different stages of cellular growth or between normal and diseased states. Recently, changes in gene expression have also been used to assess the activity of new drug candidates and to identify new targets for drug development. The latter objective is accomplished by correlating the expression of a gene or genes known to be affected by a particular drug with the expression profile of other genes of unknown function when exposed to that same drug. Genes of unknown function that exhibit the same pattern of regulation, or signature, in response to the drug are likely to represent novel targets for pharmaceutical development.

DNA arrays are particularly useful in gene expression analysis at the level of transcription (see, e.g., Ramsay, *Nature Biotechnol.* 16:40-44, 1998; Marshall and Hodgson, *Nature Biotechnol.* 16:27-31, 1998; Lashkari et al., *Proc. Natl. Acad. Sci.* (*USA*) 94:130-157, 1997; DeRisi et al., *Science* 278:680-6, 1997). In such analysis, the identity and abundance of a selected nucleic acid sequence in a sample is determined by measuring the level of hybridization of the nucleic acid sequence to probes on the DNA array that comprise complementary sequences. The selected nucleic acid sequence in a sample can be an mRNA, or a nucleic acid molecule derived from an mRNA that has a nucleic acid sequence that is identical to, or complementary to, all, or a portion, of the mRNA. Using DNA array expression assays, complex mixtures of labeled nucleic acids (e.g., mRNAs, or nucleic acid molecules derived from mRNAs) can be analyzed.

The nucleic acid molecules used to screen a DNA array should be representative of the mRNA population from which they are derived. All, or substantially all, of the sequences in the mRNA population should be represented in the nucleic acid molecule population used to screen the DNA array. For example, all portions of individual mRNA molecules should be equally represented in the nucleic acid molecule population used to screen the DNA array. In this regard, the use of oligo-dT primers, that hybridize to the polyA tail of mRNA molecules, to prime the enzymatic synthesis of complementary DNA molecules, results in the underrepresentation of the 3' ends of long mRNA molecules in the population of complementary DNA molecules.

A proposed solution to this problem is to use a population of oligonucleotides, having random nucleic acid sequences, to prime the enzymatic synthesis of DNA molecules complementary to the template mRNA molecules. It is statistically likely that at least one of the random oligonucleotides will hybridize to at least one portion of each mRNA molecule in a population, thereby yielding a population of complementary DNA molecules that represent all, or substantially all, portions of all, or substantially all, mRNA molecules in the template population. A drawback to this approach, however, is that there is little or no amplification of the sequences in the template mRNA population, thereby limiting the practical usefulness of the technique, for example to produce enough probe to screen numerous DNA arrays.

Further, the nucleic acid molecules used to screen a DNA array should selectively hybridize to complementary nucleic acid molecules, and not hybridize, to a significant extent, to non-complementary nucleic acid molecules, immobilized on the DNA array. In this regard, the present inventors have observed that RNA molecules are typically more prone to hybridize to complementary nucleic acid molecules, immobilized on a DNA array, than are DNA molecules.

Thus, there is a need for methods for synthesizing DNA molecules from mRNA template molecules, wherein: (a) the synthesized DNA molecules represent all, or substantially all, portions of all, or substantially all, template mRNA molecules; (b) the abundance of each template mRNA molecule, and each portion of each template mRNA molecule, is identical, or substantially identical, to the abundance of the identical, or complementary, DNA sequence in the population of synthesized DNA molecules; and (c) the synthetic method is capable of amplifying a small amount of template mRNA (e.g., 1 µg or less) to yield sufficient probe to screen numerous DNA microarrays. Preferably, the synthesized DNA molecules selectively hybridize to complementary nucleic acid molecules, and do not hybridize, to a significant extent, to non-complementary nucleic acid molecules immobilized on a DNA array. Moreover, it is desirable that the synthetic methods controllably yield a population of DNA molecules wherein all, or substantially all, of the DNA molecules are complementary to either the sequences of the template mRNA molecules, or to the complementary sequences of the template mRNA molecules.

In one aspect, the present invention provides processed nucleic acid samples that meet the foregoing requirements, and methods for making such processed nucleic acid samples.

SUMMARY OF THE INVENTION

In accordance with the foregoing, in one aspect the present invention provides methods of synthesizing a preparation of nucleic acid molecules, the methods comprising the steps of: (a) utilizing an RNA template to enzymatically synthesize a first DNA molecule that is complementary to at least 50 contiguous bases of the RNA template; (b) utilizing the first DNA molecule as a template to enzymatically synthesize a second DNA molecule, thereby forming a double-stranded DNA molecule wherein the first DNA molecule is hybridized to the second DNA molecule; (c) utilizing the first or second DNA molecule of the double-stranded DNA molecule as a template to enzymatically synthesize a first RNA molecule that is complementary to either the first DNA molecule or to the second DNA molecule; and (d) utilizing the first RNA molecule as a template to enzymatically synthesize a third DNA molecule that is complementary to the first RNA molecule. The double-stranded DNA molecule prepared in accordance with step (b) can optionally be enzymatically amplified before utilizing the first, or second, DNA molecule of the double-stranded DNA molecule as a template to enzymatically synthesize a first RNA molecule. The third DNA molecule prepared in accordance with the methods of this aspect of the invention can be labeled with a dye. In some embodiments of the methods of this aspect of the invention, the third DNA molecule is labeled via an aminoallyl linkage. The methods of this aspect of the invention yields populations of third DNA molecules that are representative of the population of RNA template molecules used to synthesize the third DNA molecules. In particular, substantially all of the RNA molecules in the population of template RNA molecules are represented in the population of third DNA molecules, and there is substantially no 5' or 3' bias within the population of third DNA molecules. The embodiments of the methods of this aspect of the invention that include amplification of the double-stranded DNA molecules typically yield an amount of third DNA molecules that is at least a thousand-fold greater than the amount of template RNA molecules.

The methods of the invention for synthesizing a preparation of nucleic acid molecules are useful in any situation where it is desired to synthesize a preparation of nucleic acid molecules, such as DNA molecules, beginning with an RNA template. For example, the methods of this aspect of the invention are useful for synthesizing a population of third DNA molecules that is used to hybridize to a population of immobilized nucleic acid molecules, such as a population of DNA molecules immobilized on a DNA microarray. For example, third DNA molecules prepared in accordance with the methods of this aspect of the invention can be used to hybridize to a DNA chip in order to generate a gene expression profile. Gene expression profiling can be done, for example, for purposes of screening, diagnosis, staging a disease, and monitoring response to therapy, as well as for identifying genetic targets of drugs and of pathogens.

In another aspect, the present invention provides processed DNA samples prepared by a method of the invention for synthesizing a preparation of nucleic acid molecules. The processed DNA samples of the invention can be utilized in any experiment, process or therapeutic treatment that requires DNA. For example, the processed DNA samples of the invention can be hybridized to a population of immobilized nucleic acid molecules, such as to a population of DNA molecules immobilized on a Southern blot, to a population of RNA molecules immobilized on a Northern blot, or to a population of DNA molecules immobilized on a DNA microarray (such as for the purpose of gene expression profiling). For example, the processed DNA samples of the invention can be used in the gene expression profiling method set forth in Hughes, T. R., et al., Nature Biotechnology 19:342-347 (2001), which publication is incorporated herein by reference. When used as probes to hybridize to a population of immobilized nucleic acid molecules, such as a population of nucleic acid molecules immobilized on a DNA array, processed DNA samples of the invention exhibit a high level of hybridization specificity and sensitivity.

In another aspect, the present invention provides methods for hybridizing a processed DNA sample to a population of immobilized nucleic acid molecules, the methods each comprising the step of hybridizing a processed DNA sample to a population of immobilized nucleic acid molecules, wherein the processed DNA sample is prepared by a method of the invention for synthesizing a preparation of nucleic acid molecules. The methods of the invention for hybridizing a processed DNA sample to a population of immobilized nucleic acid molecules are useful in any hybridization experiment wherein DNA molecules are hybridized to a population of immobilized nucleic acid molecules, such as a population of DNA molecules immobilized on a DNA microarray.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
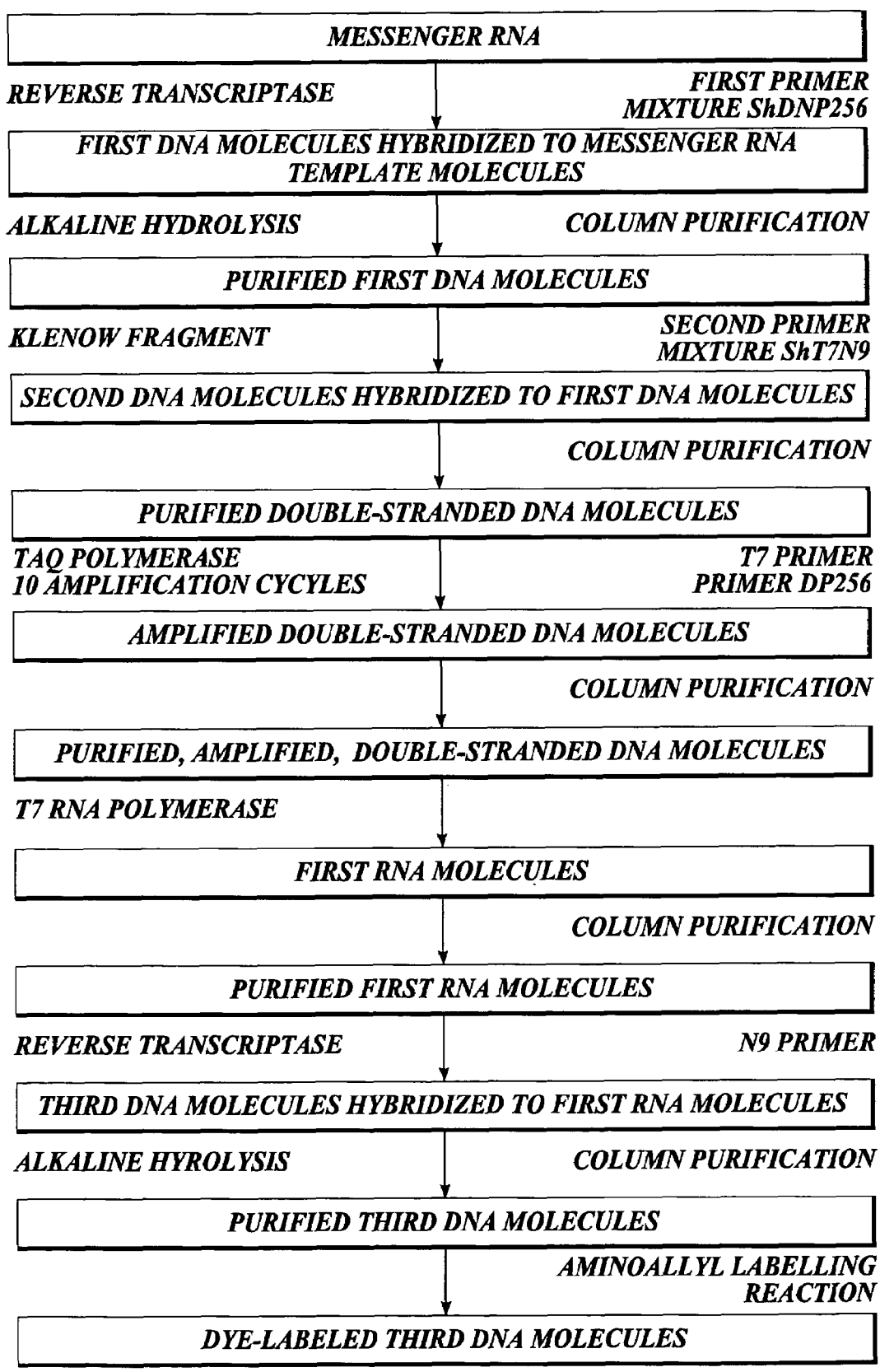
FIG. 1 shows a representative embodiment of the methods of the invention for synthesizing a preparation of nucleic acid molecules.

Unless specifically defined herein, all terms used herein have the same meaning as they would to one skilled in the art of the present invention.

In one aspect, the present invention provides methods of synthesizing a preparation of nucleic acid molecules, the methods comprising the steps of: (a) utilizing an RNA template to enzymatically synthesize a first DNA molecule that is complementary to at least 50 contiguous bases of said RNA template; (b) utilizing the first DNA molecule as a template to enzymatically synthesize a second DNA molecule, thereby forming a double-stranded DNA molecule wherein the first DNA molecule is hybridized to the second DNA molecule; (c) utilizing the first or second DNA molecule of the double-stranded DNA molecule as a template to enzymatically synthesize a first RNA molecule that is complementary to either the first DNA molecule or to the second DNA molecule; and (d) utilizing the first RNA molecule as a template to enzymatically synthesize a third DNA molecule that is complementary to the first RNA molecule. The double-stranded DNA molecule prepared in accordance with step (b) can optionally be enzymatically amplified before utilizing the first, or second, DNA molecule of the double-stranded DNA molecule as a template to enzymatically synthesize a first RNA molecule. The third DNA molecule prepared in accordance with the methods of this aspect of the invention can be labeled with a dye. In some embodiments of the methods of this aspect of the invention, the third DNA molecule is labeled via an aminoallyl linkage.

Preparation of RNA molecules useful as templates. RNA molecules useful as templates in the methods of this aspect of the invention can be isolated from any organism or part thereof, including organs, tissues, and/or individual cells. Any suitable RNA preparation can be utilized, such as total cellular RNA, or such as cytoplasmic RNA or such as an RNA preparation that is enriched for messenger RNA (mRNA), such as RNA preparations that include greater than 70%, or greater than 80%, or greater than 90%, or greater than 95%, or greater than 99% messenger RNA. Typically, RNA preparations that are enriched for messenger RNA are utilized to provide the RNA template in the practice of the methods of this aspect of the invention. Messenger RNA can be purified in accordance with any art-recognized method, such as by the use of oligo-dT columns (see, e.g., Sambrook et al., 1989,

*Molecular Cloning—A Laboratory Manual* (2nd Ed.), Vol. 1, Chapter 7, Cold Spring Harbor Laboratory, Cold Spring Harbor, N.Y.).

RNA may be isolated from eukaryotic cells by procedures that involve lysis of the cells and denaturation of the proteins contained therein. Cells of interest include wild-type cells, drug-exposed wild-type cells, modified cells, and drug-exposed modified cells.

Additional steps may be employed to remove DNA. Cell lysis may be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin et al., 1979, *Biochemistry* 18:5294-5299). Messenger RNA is selected by selection with oligo-dT cellulose (see Sambrook et al., supra). Separation of RNA from DNA can also be accomplished by organic extraction, for example, with hot phenol or phenol/chloroform/isoamyl alcohol.

If desired, RNase inhibitors may be added to the lysis buffer. Likewise, for certain cell types, it may be desirable to add a protein denaturation/digestion step to the protocol.

The sample of RNA can comprise a plurality of different mRNA molecules, each different mRNA molecule having a different nucleotide sequence. In a specific embodiment, the mRNA molecules in the RNA sample comprise at least 100 different nucleotide sequences. In other embodiments, the mRNA molecules of the RNA sample comprise at least 500, 1,000, 5,000, 10,000, 20,000, 30,000, 40,000, 50,000, 60,000, 70,000, 80,000 90,000 or 100,000 different nucleotide sequences. In another specific embodiment, the RNA sample is a mammalian RNA sample, the mRNA molecules of the mammalian RNA sample comprising about 20,000 to 30,000 different nucleotide sequences.

Synthesis of first DNA molecules. In the practice of the methods of this aspect of the invention, DNA molecules, referred to herein as first DNA molecules, are synthesized that are complementary to the RNA template molecules. Individual first DNA molecules can be complementary to a whole RNA template molecule, or to a portion thereof. For example, a first DNA molecule can be complementary to the portion of a template RNA molecule that extends from the 3' end of the template RNA molecule to the midpoint of the template RNA molecule; similarly, by way of example, a first DNA molecule can be complementary to the portion of an RNA template molecule that extends from the 5' end of the RNA molecule to the midpoint of the RNA molecule. Many first DNA molecules are complementary to at least 50 contiguous bases of an RNA template molecule. Thus, in this example, the complete complementary sequence of a RNA template molecule is represented in the population of first DNA molecules; the 5' half of the complementary sequence is represented on one DNA molecule, and the 3' half of the complementary sequence is represented on another DNA molecule.

Thus, in the practice of the methods of this aspect of the invention, a population of first DNA molecules is synthesized that includes individual DNA molecules that are each complementary to all, or to a portion, of a template RNA molecule. Typically, at least a portion of the complementary sequence of at least 95% (more typically at least 99%) of the template RNA molecules are represented in the population of first DNA molecules. Of the template RNA molecules that are represented in the population of first DNA molecules, typically at least 95% (more typically at least 98%) of the complementary sequence of each represented template RNA molecule is present in the population of first DNA molecules.

Any reverse transcriptase molecule can be utilized to synthesize the first DNA molecules, such as those derived from Moloney murine leukemia virus (MMLV-RT), avian myeloblastosis virus (AMV-RT), bovine leukemia virus (BLV-RT), Rous sarcoma virus (RSV) and human immunodeficiency virus (HIV-RT). A reverse transcriptase lacking RNaseH activity (e.g., SUPERSCRIPT II™ sold by Stratagene, La Jolla, Calif.) is preferred, however, because, in the absence of an RNaseH activity, synthesis of the second DNA molecules does not occur during synthesis of the first DNA molecules, thereby preventing incorporation of the first primer sequence(s) into the second DNA molecules. The reverse transcriptase molecule should also preferably be thermostable so that the first strand synthesis reaction can be conducted at as high a temperature as possible, while still permitting hybridization of the first primer(s) to the RNA template molecules. In some embodiments of the methods of this aspect of the invention, in order to minimize the amount of double-stranded DNA synthesized during the synthesis of the first DNA molecules, a reverse transcriptase that lacks RNase H activity is utilized, and the duration of the first DNA molecules synthesis reaction is less than two hours (such as between 20 minutes and two hours, or between 15 minutes and 25 minutes).

Priming the synthesis of the first DNA molecules. The synthesis of the first DNA molecules is primed using any suitable primer, typically an oligonucleotide in the range of ten to 60 bases in length. The nucleic acid sequence of the oligonucleotide used to prime the synthesis of the first DNA molecules is therefore incorporated into the sequence of each, synthesized, first DNA molecule. Oligonucleotides that are useful for priming the synthesis of the first DNA molecules can hybridize to any portion of the RNA template molecules, including the oligo-dT tail. In some embodiments, the synthesis of the first DNA molecules is primed using a first primer mixture comprising a multiplicity of first primers, wherein each of the first primers includes a random sequence portion, and a defined sequence portion. The random sequence portion comprises a random sequence of nucleic acid residues. Statistically, it is likely that most, or all, of the random sequences are sufficiently complementary to a portion of one or more RNA template molecules, to be able to hybridize thereto under the conditions utilized to hybridize the first primer molecules to the RNA template molecules. The random sequence portion typically consists of from four to 20 nucleic acid residues, such as from four to 15 nucleic acid residues, such as from six to nine nucleic acid residues. In one embodiment, the random sequence portion consists of nine nucleic acid residues. Typically, the defined sequence portion is located 5' to the random sequence portion.

The defined sequence portion of the first primers comprises a known sequence of nucleic acid residues, and can include an RNA polymerase promoter. The RNA polymerase promoter sequence is therefore incorporated into the sequence of the first DNA molecules, which can thereafter be utilized as templates for the synthesis of RNA molecules that are complementary in sequence to the first DNA molecules. Any RNA polymerase promoter sequence can be included in the defined sequence portion of the first primers. Representative examples of useful RNA polymerase promoters include a T7 RNA polymerase promoter and an SP6 RNA polymerase promoter. A representative defined sequence portion of a first primer that includes a T7 RNA polymerase promoter sequence is 5' ACTA TAG GGA GA 3' (SEQ ID NO:1), which is the defined sequence portion of representative first primer molecule ShT7N9 5' ACTA TAG GGA GAN NNN NNN NN 3' (SEQ ID NO:2).

The nucleic acid sequence of an exemplary primer useful for priming the synthesis of the first DNA molecule, and which does not include an RNA polymerase promoter sequence, is 5' TAG ATG CTG TTG NNN NNN NNN 3' (SEQ ID NO:3), which is called primer ShDNP256. The defined sequence portion of ShDNP256 is 5' TAG ATG CTG TTG 3' (SEQ ID NO:4).

In some embodiments, the synthesis of the first DNA molecules is primed using a mixture of primers, wherein the mixture includes poly-dT primers that each comprise a poly-dT portion and a defined sequence portion, wherein the poly-dT portion is located 5' to the defined sequence portion. The poly-dT portion of each poly-dT primer typically consists of from five to 25 nucleic acid residues, such as from 15-25 nucleic acid residues, such as 18 nucleic acid residues. In some embodiments, the poly-dT primers are used with a first primer mixture comprising a multiplicity of first primers, wherein each of the first primers comprises a random sequence portion and a defined sequence portion. The nucleic acid sequence of the defined sequence portion of the poly-dT primer is typically identical to the nucleic acid sequence of the defined sequence portion of the primers of the first primer mixture. In this way, every first DNA molecule includes the same defined sequence portion which can subsequently be utilized, for example, as a hybridization target for a primer that primes the synthesis of a complementary DNA molecule, or, for example, as an RNA polymerase promoter. Thus, in some embodiments, the defined sequence portion of the poly-dT primer comprises an RNA polymerase promoter, such as a T7 RNA polymerase promoter, such as the T7 RNA polymerase promoter having the nucleic acid sequence set forth in SEQ ID NO:1.

Hybridization of oligonucleotide primers. The following remarks describe conditions for hybridizing oligonucleotide primers to target nucleic acid molecules, such as hybridizing first primers to mRNA molecules in the practice of the synthetic methods of the invention.

Typically, for oligonucleotide molecules less than 100 bases in length, hybridization conditions are 5 to 10° C. below the homoduplex melting temperature (Tm); see generally, Sambrook et al. *Molecular Cloning: A Laboratory Manual*, 2nd ed., Cold Spring Harbor Press, 1987; Ausubel et al., *Current Protocols in Molecular Biology*, Greene Publishing, 1987).

Preparing oligonucleotides useful as primers. The following remarks describe representative methods and compositions useful for making any oligonucleotide primer utilized in the practice of the present invention, including oligonucleotides useful for priming synthesis of the first DNA molecules.

A primer may be prepared by any suitable method, such as phosphotriester and phosphodiester methods of synthesis, or automated embodiments thereof. It is also possible to use a primer that has been isolated from a biological source, such as a restriction endonuclease digest.

An oligonucleotide primer can be DNA, RNA, chimeric mixtures or derivatives or modified versions thereof, so long as it is still capable of priming the desired reaction. The oligonucleotide primer can be modified at the base moiety, sugar moiety, or phosphate backbone, and may include other appending groups or labels, so long as it is still capable of priming the desired amplification reaction.

For example, an oligonucleotide primer may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5N-methoxycarboxymethyluracil, 5-methoxyuracil, 2-methylthio-N-6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, 5-methyl-2-thiouracil, 3-(3-amino-3-N-2-carboxypropyl) uracil, and 2,6-diaminopurine.

In another embodiment, the oligonucleotide primer comprises at least one modified sugar moiety selected from the group including but not limited to arabinose, 2-fluoroarabinose, xylulose, and hexose.

In yet another embodiment, the oligonucleotide primer comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal, or analog thereof.

An oligonucleotide primer for use in the methods of the invention may be derived by cleavage of a larger nucleic acid fragment using non-specific nucleic acid cleaving chemicals or enzymes or site-specific restriction endonucleases; or by synthesis by standard methods known in the art, e.g., by use of an automated DNA synthesizer (such as are commercially available from Biosearch, Applied Biosystems, etc.) and standard phosphoramidite chemistry. As examples, phosphorothioate oligonucleotides may be synthesized by the method of Stein et al. (*Nucl. Acids Res.* 16:3209-3221, 1988), methylphosphonate oligonucleotides can be prepared by use of controlled pore glass polymer supports (Sarin et al., 1988, *Proc. Natl. Acad. Sci. U.S.A.* 85:7448-7451).

Once the desired oligonucleotide is synthesized, it is cleaved from the solid support on which it was synthesized and treated, by methods known in the art, to remove any protecting groups present. The oligonucleotide may then be purified by any method known in the art, including extraction and gel purification. The concentration and purity of the oligonucleotide may be determined by examining oligonucleotide that has been separated on an acrylamide gel, or by measuring the optical density at 260 nm in a spectrophotometer.

Hydrolysis of template RNA molecules and removal of first primers. In some embodiments, the RNA template molecules are hydrolyzed, and all, or substantially all (typically more than 99%), of the first primers are removed, after synthesis of the first DNA molecules, and before synthesis of the second DNA molecules. Hydrolysis of the RNA template can be achieved, for example, by alkalinization of the solution containing the RNA template (e.g., by addition of an aliquot of a concentrated sodium hydroxide solution). The primers can be removed, for example, by applying the solution containing the RNA template molecules, first DNA molecules, and the first primers, to a column that separates nucleic acid molecules on the basis of size. The purified, first DNA molecules, can then, for example, be precipitated and redissolved in a suitable buffer for the next step of the methods of this aspect of the invention.

Synthesis of the second DNA molecules. In the practice of the methods of the invention, DNA molecules, referred to herein as second DNA molecules, are synthesized that are complementary to the first DNA molecules. Individual second DNA molecules can be complementary to a whole first DNA molecule, or to a portion thereof. For example, a second DNA molecule can be complementary to a portion of a first DNA molecule that is located between the 3' end of the first DNA molecule and the midpoint of the first DNA molecule; similarly, by way of example, a second DNA molecule can be complementary to a portion of a first DNA molecule that is located between the 5' end of the first DNA molecule and the midpoint of the first DNA molecule. Typically, second DNA molecules are each complementary to at least 50 contiguous bases of a first DNA molecule.

Thus, in the practice of the methods of this aspect of the invention, a population of second DNA molecules is synthesized that includes individual second DNA molecules that are each complementary to all, or to a portion, of a first DNA molecule. Typically, at least a portion of the complementary sequence of at least 95% (more typically at least 98%, such as at least 99%) of the first DNA molecules are represented in the population of second DNA molecules. Of the first DNA molecule complementary sequences that are represented in the population of second DNA molecules, typically at least 95% (more typically at least 98%, such as at least 99%) of the complementary sequence of each represented first DNA molecule is present in the population of second DNA molecules.

A DNA-dependent, DNA polymerase is utilized to synthesize the second DNA molecules. For example, the Klenow fragment of DNA polymerase I can be utilized to synthesize the second DNA molecules. The synthesis of the second DNA molecules is primed using any suitable primer or primers, provided that the primer(s) used to prime synthesis of the second DNA molecules does not have the same nucleic acid sequence as the primer(s) used to prime the synthesis of the first DNA molecules. In this way, both the first and the second DNA molecules include a unique primer sequence. The unique primer sequence included in the first DNA molecules is not included in the second DNA molecules, and the unique primer sequence that is included in the second DNA molecules is not included in the first DNA molecules. Depending on the choice of primer sequence, these unique primer sequences can be used, for example, to selectively direct DNA-dependent RNA synthesis from either the first or the second DNA molecules or, for example, to selectively direct DNA-dependent DNA synthesis from either the first DNA molecules, or from the second DNA molecules.

In some embodiments, the synthesis of the second DNA molecules is primed using a second primer mixture comprising a multiplicity of second primer molecules, wherein each second primer molecule comprises a random sequence portion and a defined sequence portion. The defined sequence portion is located 5' to the random sequence portion. The sequence of the defined sequence portion of the second primer molecules is not present in the sequence of the first primer molecules. Thus, for example, the defined sequence portion of the second primer molecules can include the nucleic acid sequence of an RNA polymerase promoter, such as a T7 RNA polymerase promoter, such as the sequence of the T7 RNA polymerase promoter set forth in SEQ ID NO:1. A representative nucleic acid sequence of a first primer molecule, called ShT7N9, that includes a defined sequence portion including a T7 promoter sequence is set forth in SEQ ID NO:2.

An example of a primer, that does not include an RNA polymerase promoter sequence, useful for priming the synthesis of the second DNA molecules is set forth in SEQ ID NO:3, which shows the nucleic acid sequence of primer ShDNP256.

Thus, in one representative embodiment of the methods of the invention, the defined sequence portion of the first primer mixture includes an RNA polymerase promoter (such as the T7 RNA polymerase sequence set forth in SEQ ID NO:1), and the defined sequence portion of the second primer mixture does not include an RNA polymerase promoter sequence. Again, by way of representative example, in one embodiment of the methods of the invention, the defined sequence portion of the second primer mixture includes an RNA polymerase promoter sequence (such as the T7 RNA polymerase promoter sequence set forth in SEQ ID NO:1), and the defined sequence portion of the first primer mixture does not include an RNA polymerase promoter sequence.

Oligonucleotides useful for priming synthesis of the second DNA molecules can be made using any art-recognized method, such as by utilizing the methods and compositions described herein under the heading "Preparing oligonucleotides useful as primers."

In some embodiments of the methods of this aspect of the invention, the reaction time for the synthesis of the second DNA molecules is from about 45 minutes to about sixty minutes.

Purification of double-stranded DNA molecules. Synthesis of the second DNA molecules yields a population of double-stranded DNA molecules wherein the first DNA molecules are hybridized to the second DNA molecules. Typically, the double-stranded DNA molecules are purified to remove substantially all nucleic acid molecules shorter than 100 base pairs, including all, or substantially all (i.e., typically more than 99%), of the second primers. Purification can be achieved by any art-recognized means, such as by elution through a size-fractionation column. The purified, second DNA molecules can then, for example, be precipitated and redissolved in a suitable buffer for the next step of the methods of this aspect of the invention.

Amplification of the double-stranded DNA molecules. In the practice of the methods of this aspect of the invention, either the first DNA molecules or the second DNA molecules of the double-stranded DNA molecules are utilized as templates to enzymatically synthesize first RNA molecules that are complementary in sequence to either the first DNA molecules or to the second DNA molecules (i.e., complementary to the template DNA molecules). Typically, however, before synthesis of the first RNA molecules, the double-stranded DNA molecules are enzymatically amplified using the polymerase chain reaction. Any suitable primers can be used to prime the polymerase chain reaction. Typically, two primers are used; one primer hybridizes to the defined portion of the first primer sequence (or to the complement thereof), and the other primer hybridizes to the defined portion of the second primer sequence (or to the complement thereof).

Thus, for example, the highlighted portion of the T7 primer sequence 5' AAT TAA TAC GAC TCA CTA TAG GGA GA 3' (SEQ ID NO:5) is identical to the highlighted portion of the ShT7N9 primer sequence 5' ACTA TAG GGA GAN NNN NNN NN 3' (SEQ ID NO:2). Under appropriate hybridization conditions, the highlighted portion of the T7 primer (SEQ ID NO:5) will hybridize to the complement of the highlighted portion of the ShT7N9 primer sequence (SEQ ID NO:2). Thus, in a PCR amplification reaction, the T7 primer (SEQ ID NO:5) can be used to prime synthesis of a first or second DNA molecule that includes the complement of the ShT7N9 primer sequence (SEQ ID NO:2).

Similarly, the highlighted portion of the DP256 primer 5' GTT CGA GAC CTC TAG ATG CTG TTG 3' (SEQ ID NO:6) is identical to the highlighted portion of the ShDNP256 primer 5' TAG ATG CTG TTG NNN NNN NNN 3' (SEQ ID NO:3). Thus, in a PCR amplification reaction, the highlighted portion of the DP256 primer (SEQ ID NO:6) can be used to prime synthesis of a first or second DNA molecule that includes the complement of the highlighted portion of the ShDNP256 primer sequence (SEQ ID NO:3).

In general, the greater the number of amplification cycles during the polymerase chain reaction, the greater the amount of amplified DNA that is obtained. On the other hand, too many amplification cycles may result in randomly biased amplification of the double-stranded DNA. Thus, for example, if a sample of purified messenger RNA is split into two identical portions, and each portion is utilized as template to synthesize double-stranded DNA in accordance with the methods of the invention, and too many amplification cycles are utilized during the polymerase chain reaction step; then the composition of the amplified, double-stranded, DNA derived from the two identical portions of the RNA sample may be significantly different. Thus, in some embodiments, a desirable number of amplification cycles is between one and 25 amplification cycles, such as from five to 15 amplification cycles, such as ten amplification cycles. Where an amplification step is included in the methods of the invention, the amplified, double-stranded, DNA is typically purified to remove nucleic acid molecules consisting of less than about 100 base pairs. By way of example, purification can be achieved by the use of a size-fractionation column.

In some embodiments of the methods of this aspect of the invention, from about 100 nanograms (ng) to about 200 ng of the double-stranded DNA molecules are used as substrate in a PCR amplification reaction.

Synthesis of the first RNA molecules. In the practice of the methods of the invention, either the first DNA molecules or the second DNA molecules of the double-stranded DNA molecules are utilized as templates to enzymatically synthesize first RNA molecules that are complementary in sequence to either the first DNA molecules or to the second DNA molecules (i.e., complementary to the template DNA molecules). The RNA synthesis reaction is catalyzed by an RNA polymerase. Representative examples of useful RNA polymerase molecules include the SP6 RNA polymerase and the T7 RNA polymerase. The first or second DNA molecules that are used as the templates for synthesis of the first RNA molecules includes an RNA polymerase promoter sequence that was introduced during synthesis of the first or second DNA molecules. The RNA polymerase promoter sequence was included in the sequence of the primer(s) used to prime synthesis of the first or second DNA molecules. For example, primer ShT7N9, having the nucleic acid sequence set forth in SEQ ID NO:2, includes the sequence of a T7 RNA polymerase promoter (SEQ ID NO:1). Thus, if primer ShT7N9 (SEQ ID NO:2) is utilized to prime the synthesis of the first DNA molecules, then each of the first DNA molecules includes the sequence of the T7 RNA polymerase promoter (SEQ ID NO:1) included within primer ShT7N9 (SEQ ID NO:2), and this T7 RNA polymerase promoter (SEQ ID NO:1) can subsequently be utilized to promote the synthesis of a population of RNA molecules that are complementary in sequence to the population of first DNA molecules.

The first RNA molecules are typically purified to remove nucleic acid molecules less than 100 bases long. Purification can be achieved by any art-recognized means, such as by the use of a size-fractionation column.

In some embodiments of the methods of this aspect of the invention, from 400 ng to 600 ng (such as about 500 ng) of amplified, double-stranded, DNA molecules are utilized as template for the synthesis of the first RNA molecules.

Synthesis of the third DNA molecules. In the practice of the methods of the invention, DNA molecules, referred to herein as third DNA molecules, are synthesized that are complementary to the first RNA molecules. Individual third DNA molecules can be complementary to a whole first RNA molecule, or to a portion thereof. For example, a third DNA molecule can be complementary to a portion of a first RNA molecule that is located between the 3' end of the first RNA molecule and the midpoint of the first RNA molecule; similarly, by way of example, a third DNA molecule can be complementary to a portion of a first RNA molecule that is located between the 5' end of the first RNA molecule and the midpoint of the first RNA molecule. Typically, third DNA molecules are each complementary to at least 50 contiguous bases of a first RNA molecule.

Thus, in the practice of the methods of this aspect of the invention, a population of third DNA molecules is synthesized that includes individual DNA molecules that are each complementary to all, or to a portion, of a first RNA molecule. Typically, at least a portion of the complementary sequence of at least 95% (more typically at least 98%, such as at least 99%) of the first RNA molecules are represented in the population of third DNA molecules. Of the complementary sequences of first RNA molecules that are represented in the population of third DNA molecules, typically at least 95% (more typically at least 98%) of the complementary sequence of each represented first RNA molecule is present in the population of third DNA molecules.

The synthesis of the third DNA molecules is catalyzed by a reverse transcriptase molecule, preferably a reverse transcriptase molecule that does not possess an RNAse H enzymatic activity (e.g., SUPERSCRIPT II™), thereby preventing the synthesis of DNA molecules that are complementary in sequence to the third DNA molecules. The synthesis of the third DNA molecule can be primed by any suitable primer, or mixture of suitable primers. In some embodiments, the synthesis of the third DNA molecule is primed using a population of random primers, wherein substantially all of the random primers consist of a random sequence of nine bases.

In some embodiments of the methods of this aspect of the invention, about 3 µg of first RNA molecules are utilized as template for the synthesis of the third DNA molecules.

Hydrolysis of the first RNA molecules and removal of primers. In some embodiments, the first RNA molecules are hydrolyzed, and all, or substantially all (typically more than 99%), of the primers are removed, after synthesis of the third DNA molecules. Hydrolysis of the first RNA molecules can be achieved, for example, by alkalinization of the solution containing the RNA template (e.g., by addition of an aliquot of a concentrated sodium hydroxide solution). The primers can be removed, for example, by applying the solution containing the first RNA molecules, third DNA molecules, and the primers, to a column that separates nucleic acid molecules on the basis of size. The purified, third DNA molecules, can then be precipitated and redissolved in a suitable buffer for the next step of the methods of this aspect of the invention.

Labelling the third DNA molecules with a dye. Optionally, the third DNA molecules can be labeled with a dye molecule to facilitate the detection of the third DNA molecules when they are used as a probe in a hybridization experiment, such as a probe used to screen a DNA chip. Any suitable dye molecules can be utilized, provided that they are attached to the third DNA molecules by aminoallyl linkages. Examples of suitable dyes include fluorophores and chemiluminescers.

By way of example, third DNA molecules can be coupled to dye molecules via aminoallyl linkages by incorporating allylamine-derivatized nucleotides (e.g., allylamine-dATP, allylamine-dCTP, allylamine-dGTP, and/or allylamine-dTTP) into the third DNA molecules during synthesis of the third DNA molecules. The allylamine-derivatized nucleotide(s) can then be coupled, via an aminoallyl linkage, to N-hydroxysuccinimide ester derivatives (NHS derivatives) of dyes (e.g., Cy-NHS, Cy3-NHS and/or Cy5-NHS). Again by way of example, in another embodiment, dye-labeled nucleotides may be incorporated into the third DNA molecules during synthesis of the third DNA molecules, which labels the third DNA molecules directly.

It is also possible to include a spacer (usually 5-16 carbon atoms long) between the dye and the nucleotide, which may improve enzymatic incorporation of the modified nucleotides during synthesis of the third DNA molecules.

Representative examples of useful fluorophores are as follows:
  4-acetamido-4'-isothiocyanatostilbene-2,2'disulfonic acid
  acridine and derivatives:
  acridine
  acridine isothiocyanate
  5-(2'-aminoethyl)aminonaphthalene-1-sulfonic acid (EDANS)
  4-amino-N-[3-vinylsulfonyl)phenyl]naphthalimide-3,5 disulfonate (Lucifer Yellow VS)
  anthranilamide
  Brilliant Yellow
  coumarin and derivatives:
  coumarin
  7-amino-4-methylcoumarin (AMC, Coumarin 120)
  7-amino-4-trifluoromethylcoumarin (Coumarin 151)
  Cy3
  Cy5
  cyanosine
  4',6-diaminidino-2-phenylindole (DAPI)
  5',5"-dibromopyrogallol-sulfonephthalein (Bromopyrogallol Red)
  7-diethylamino-3-(4'-isothiocyanatophenyl)-4-methylcoumarin
  diethylenetriamine pentaacetate
  4,4'-diisothiocyanatodihydro-stilbene-2,2'-disulfonic acid
  4,4'-diisothiocyanatostilbene-2,2'-disulfonic acid
  5-[dimethylamino]naphthalene-1-sulfonyl chloride (DNS, dansyl chloride)
  4-(4'-dimethylaminophenylazo)benzoic acid (DABCYL)
  4-dimethylaminophenylazophenyl-4'-isothiocyanate (DABITC)
  eosin and derivatives:
  eosin
  eosin isothiocyanate
  erythrosin and derivatives:
  erythrosin B
  erythrosin isothiocyanate
  ethidium
  fluorescein and derivatives:
  5-carboxyfluorescein (FAM)
  5-(4,6-dichlorotriazin-2-yl) aminofluorescein (DTAF)
  2'7'-dimethoxy-4'5'-dichloro-6-carboxyfluorescein (JOE)
  fluorescein
  fluorescein isothiocyanate
  QFITC (XRITC)
  fluorescamine
  IR144
  IR1446
  Malachite Green isothiocyanate
  4-methylumbelliferone
  ortho cresolphthalein
  nitrotyrosine
  pararosaniline
  Phenol Red
  B-phycoerythrin
  o-phthaldialdehyde
  pyrene and derivatives:
  pyrene
  pyrene butyrate
  succinimidyl 1-pyrene butyrate
  Reactive Red 4 (Cibacron7 Brilliant Red 3B-A)
  rhodamine and derivatives:
  6-carboxy-X-rhodamine (ROX)
  6-carboxyrhodamine (R6G)
  lissamine rhodamine B sulfonyl chloride
  rhodamine (Rhod)
  rhodamine B
  rhodamine 110
  rhodamine 123
  rhodamine X isothiocyanate
  sulforhodamine B
  sulforhodamine 101
  sulfonyl chloride derivative of sulforhodamine 101 (Texas Red)
  N,N,N',N'-tetramethyl-6-carboxyrhodamine (TAMRA)
  tetramethyl rhodamine
  tetramethyl rhodamine isothiocyanate (TRITC)
  riboflavin
  rosolic acid
  terbium chelate derivatives Representative method of the invention. FIG. 1 shows a representative method of the present invention. In the method disclosed in the FIG. 1, a population of messenger RNA molecules are used as templates to synthesize first DNA molecules, thereby yielding double-stranded molecules in which a messenger RNA molecule is hybridized to a complementary first DNA molecule. The synthesis of first DNA molecules is catalyzed by reverse transcriptase, and the reaction is primed by a first primer mixture, which includes a multiplicity of first primer molecules (called ShDNP256) that each have the nucleic acid sequence shown in SEQ ID NO:3. Each of the first primer molecules (SEQ ID NO:3) includes a defined sequence portion and a random sequence portion. The defined sequence portion is located 5' to the random sequence portion. The nucleic acid sequence of the defined sequence portion is set forth in SEQ ID NO:4. Thus, the nucleic acid sequence set forth in SEQ ID NO:4 is incorporated into each first DNA molecule.

The sequence of the random sequence portion of each first primer molecule (SEQ ID NO:3) is different from the sequence of the random sequence portion of substantially every other first primer molecule (SEQ ID NO:3). Thus, it is statistically likely that at least one first primer molecule (SEQ ID NO:3) will hybridize to every messenger RNA molecule within the population of messenger RNA molecules. More than one first primer molecule (SEQ ID NO:3) may hybridize to a single, template, messenger RNA molecule, thereby permitting the synthesis of more than one first DNA molecule corresponding to more than one portion of the template messenger RNA molecule. Thus, the complementary sequence of every portion, or almost every portion, of every messenger RNA molecule, or almost every messenger RNA molecule, in the population of messenger RNA molecules is represented within the population of first DNA molecules.

The population of double-stranded nucleic acid molecules, that each include a first DNA molecule hybridized to a messenger RNA template molecule, is then hydrolyzed under alkaline conditions to degrade the messenger RNA molecules. The hydrolyzed mixture is then applied to a column that separates nucleic acid molecules on the basis of size. In this way, nucleic acid molecules of less than 100 base pairs are removed from the population of first DNA molecules. The purified first DNA molecules are then utilized as templates to enzymatically synthesize second DNA molecules. The synthesis of the second DNA molecules is catalyzed by the Klenow fragment of DNA polymerase I, and the synthesis of the second strand DNA molecules is primed using a second primer mixture that includes a multiplicity of second primer molecules (called ShT7N9 (SEQ ID NO:2)) which each include a defined sequence portion (SEQ ID NO:1) and a random sequence portion, wherein the defined sequence portion (SEQ ID NO:1) is located 5' to the random sequence portion.

Thus, each second DNA molecule incorporates at least one ShT7N9 defined sequence portion (SEQ ID NO:1). The product of the second DNA molecule synthesis reaction is a double-stranded DNA molecule in which a second DNA molecule is hybridized to a complementary first DNA molecule. Nucleic acid molecules of less than 100 bases are separated from the population of double-stranded DNA molecules by elution from a column that separates nucleic acid molecules on the basis of size. The resulting, purified, double-stranded DNA molecules are then amplified using the polymerase chain reaction (PCR). The PCR reaction is catalyzed by the Taq polymerase and the reaction is primed by the T7 primer (SEQ ID NO:5) and primer DP256 (SEQ ID NO:6), which hybridize to the complement of the defined sequence portion (SEQ ID NO:1) of primer ShT7N9 (SEQ ID NO:2), and to the complement of the defined sequence portion (SEQ ID NO:4) of primer ShDNP256 (SEQ ID NO:3), respectively. In the embodiment of the methods shown in FIG. 1, the purified, double-stranded, DNA molecules are subjected to ten rounds of PCR amplification. The amplified, double-stranded, DNA molecules are then purified to remove nucleic acid molecules of less than about 100 bases. Purification is achieved using a column that separates nucleic acid molecules on the basis of size.

The second DNA molecules of the purified, amplified, double-stranded DNA molecules are then utilized as templates to synthesize a population of first RNA molecules. Each of the first RNA molecules is, therefore, complementary to a second DNA molecule, or to a portion of a second DNA molecule. The synthesis of the first RNA molecules is catalyzed by T7 RNA polymerase that utilizes the T7 promoter, included in the defined sequence portion (SEQ ID NO:1) of primer ShT7N9 (SEQ ID NO:2), that is incorporated into the second DNA molecules during their synthesis. The first RNA molecules are purified by absorption onto a column, that specifically absorbs RNA, and elution therefrom.

The purified first RNA molecules are then used as templates to synthesize a population of third DNA molecules. The synthesis of the third DNA molecules is catalyzed by reverse transcriptase and the reaction is primed by a population of random 9-mer oligonucleotides (SEQ ID NO:7). The product of the third DNA molecule synthesis reaction is a population of double-stranded nucleic acid molecules in which the first RNA molecules are hybridized to the third DNA molecules. The double-stranded nucleic acid hybrid is subjected to alkaline hydrolysis to hydrolyze the first RNA molecules. The third DNA molecules are then purified to remove nucleic acid molecules of less than about 100 bases. Purification is achieved by applying the third DNA molecule sample to a column that separates nucleic acid molecules on the basis of size.

The purified third DNA molecules are then labeled with one or more types of dye. Any useful dye can be utilized, provided that the dye is linked to the third DNA molecules by aminoally linkages.

Figure 2:
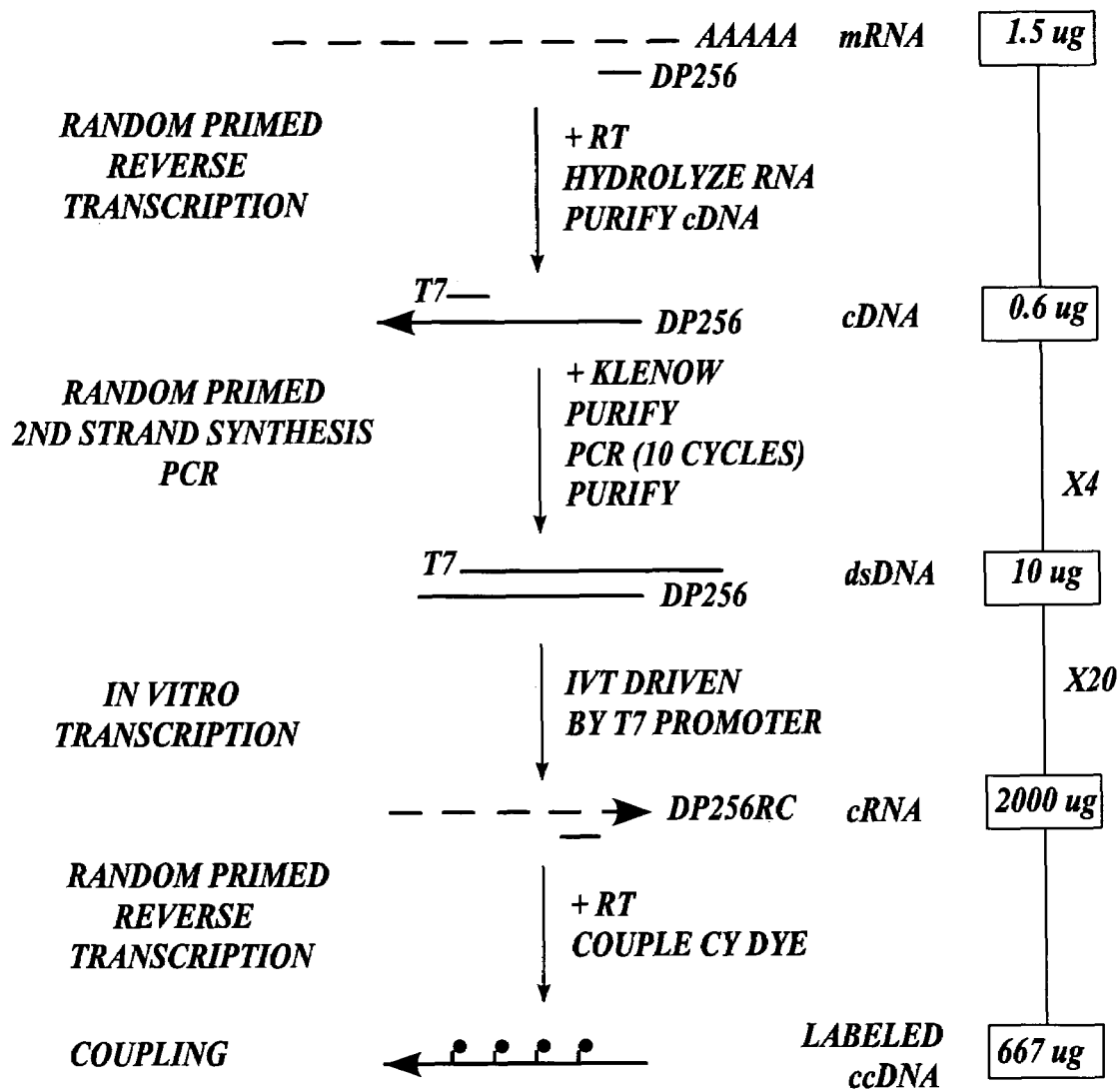
FIG. 2 shows a representative embodiment of the methods of the invention, and also shows the amplification efficiency of each step of the representative embodiment. The abbreviations are: RT, reverse transcriptase; mRNA, messenger RNA; cDNA. complementary DNA; dsDNA, double-stranded DNA; cRNA, complementary RNA; IVT, in vitro transcription. The term "coupling" refers to coupling the DNA to Cy dye molecules.

Amplification Efficiency of the methods of the invention. FIG. 2 shows a representative embodiment of the methods of the invention, and also shows the amplification efficiency of each step of the representative embodiment. Thus, the embodiment of the methods of the invention shown in FIG. 2 converts an amount of mRNA sufficient to conduct 0.5 hybridization experiments, into an amount of complementary DNA sufficient to conduct 667 hybridization experiments. The hybridization, scanning and image analysis is conducted as described in Hughes et. al., *Nature Biotechnology* 19:342-347 (2001). Hybridization experiments are conducted using oligonucleotide arrays consisting of 60-mers synthesized as described by Hughes et. al., supra.

Reproducibility and accuracy of the methods of the invention. To determine if the methods of the invention yield reproducible results, independent amplifications of a single preparation of mRNA isolated from Jurkat cells were compared. Labeled products from each amplification gave no false positives ($P<0.01$) when hybridized to a Human 25 k microarray. In addition, comparison of Jurkat and K562 samples amplified in duplicate revealed similar expression ratios when hybridized to a Human 25 k array ($r=0.99$, $P<0.01$). Perfect duplication of gene expression patterns would result in $r=1.0$.

In order to determine if tissure-specific gene expression patterns were conserved through amplification, mRNA from the human Jurkat and K562 cell lines was used to generate cDNA by a conventional, random-primed, reverse transcription method, as well as by the methods of the present invention. The expression ratios resulting from each method correlated at $r=0.95$ ($P<0.01$). Perfect duplication of gene expression patterns would result in $r=1.0$, and profiles were said to be conserved if $r>0.90$.

Representation of full-length transcripts. To determine if the methods of the invention generate cDNA representing full-length transcripts, amplification products, prepared in accordance with the methods of the invention, were hybridized to microarrays containing 60mer probes tiled across complete mRNA sequences for a number of human genes. The distribution of signal intensity consistently extended across whole transcripts, independent of transcript size and distance from the 3' end; whereas a conventional oligo dT-primed reverse transcription method resulted in a concentration of signal at the 3' end. Due to this 3' bias using conventional oligo dT-primed reverse transcription, the signal intensity often did not extend beyond the untranslated region preventing the detection of even the 3'-most coding sequences.

Nucleic acid samples of the invention. In another aspect, the present invention provides nucleic acid samples prepared in accordance with the methods of the invention. Thus, in one embodiment, the present invention provides DNA samples prepared by a method comprising the steps of: (a) utilizing an RNA template to enzymatically synthesize a first DNA molecule that is complementary to at least 50 contiguous bases of RNA template; (b) utilizing the first DNA molecule as a template to enzymatically synthesize a second DNA molecule thereby forming a double-stranded DNA molecule wherein the first DNA molecule is hybridized to the second DNA molecule; (c) utilizing the first or second DNA molecule of the double-stranded DNA molecule as a template to enzymatically synthesize a first RNA molecule that is complementary to either the first DNA molecule or to the second DNA molecule; and (d) utilizing the first RNA molecule as a template to enzymatically synthesize a third DNA molecule that is complementary to the first RNA molecule. The third DNA molecules can be linked to dye molecules by aminoallyl linkages.

In another embodiment, the present invention provides DNA samples prepared by a method comprising the steps of: (a) utilizing an RNA template to enzymatically synthesize a first DNA molecule that is complementary to at least 50 contiguous bases of the RNA template; (b) utilizing the first DNA molecule as a template to enzymatically synthesize a second DNA molecule thereby forming a double-stranded DNA molecule wherein the first DNA molecule is hybridized to the second DNA molecule; (c) enzymatically amplifying the double-stranded DNA molecule; (d) utilizing the first or second DNA molecule of the amplified, double-stranded, DNA molecule as a template to enzymatically synthesize a first RNA molecule that is complementary to either the first DNA molecule or to the second DNA molecule; and (e) utilizing the first RNA molecule as a template to enzymatically synthesize a third DNA molecule that is complementary to the first RNA molecule. The third DNA molecules can be linked to dye molecules by aminoallyl linkages.

The third DNA molecules produced by the subject methods finds use in a variety of applications. For example, third DNA molecules produced by the methods of the invention may be labeled and employed to profile gene expression in different populations of cells. In one embodiment, third DNA molecules are used for quantitative comparisons of gene expression between different populations of cells or between populations of cells exposed to different stimuli. For example, the third DNA molecules can be used in expression profiling analysis on such platforms as DNA microarrays, for construction of "driver" for subtractive hybridization assays, and the like. Especially facilitated by the subject methods are studies of differential gene expression in mammalian cells or cell populations. The cells may be from blood (e.g., white cells, such as T or B cells) or from tissue derived from solid organs, such as brain, spleen, bone, heart, vascular, lung, kidney, liver, pituitary, endocrine glands, lymph node, dispersed primary cells, tumor cells, or the like.

When used as probes to hybridize to a population of immobilized nucleic acid molecules, such as a population of nucleic acid molecules immobilized on a DNA array, DNA samples prepared in accordance with the methods of the invention exhibit a high level of hybridization specificity and sensitivity. For example, eight different transcripts were synthesized and spiked into complex mRNA samples at different ratios. Genes were selected from the yeast genome based on similarity to the physical characteristics of human genes (i.e., high GC content, ~2.0 kb length), and low potential for cross-hybridization with human sequences. The genes selected on this basis were YOR140W, YHR042W, YAL043C, YKR050W, YAL054C, YGL236C, YHL032C and YGL234W.

The coding sequences of each gene were PCR amplified from yeast genomic DNA and in vitro-transcribed to generate cRNA for spike-in experiments. These transcripts were added to mRNA from the Jurkat and K562 human cell lines at different ratios between the two samples. The RNA mixtures were then amplified and labeled according to the methods of the invention before hybridization to an array with oligonucleotides representing each transcript. For each transcript, ten 60-mers were selected and synthesized on a microarray as described by Hughes, et. al., supra. The measured expression ratios of oligonucleotides representing each transcript were averaged and plotted against the expected ratios. Accurate detection of spike-in ratios occurred at as low as 0.5 copies per cell.

Methods for hybridizing a processed DNA sample to a population of immobilized nucleic acid molecules. In another aspect, the present invention provides methods for hybridizing a processed DNA sample to a population of immobilized nucleic acid molecules. The methods of this aspect of the invention include the step of hybridizing a processed DNA sample to a population of immobilized nucleic acid molecules, wherein the processed DNA sample is prepared in accordance with a method of the present invention.

Thus, in one embodiment, the present invention provides a method for hybridizing a processed DNA sample to a population of immobilized nucleic acid molecules, the method comprising the step of hybridizing a processed DNA sample to a population of immobilized nucleic acid molecules, wherein the processed DNA sample is prepared by a method comprising the steps of: (a) utilizing an RNA template to enzymatically synthesize a first DNA molecule that is complementary to at least 50 contiguous bases of the RNA template; (b) utilizing the first DNA molecule as a template to enzymatically synthesize a second DNA molecule thereby forming a double-stranded DNA molecule wherein the first DNA molecule is hybridized to the second DNA molecule; (c) utilizing the first or second DNA molecule of the double-stranded DNA molecule as a template to enzymatically synthesize a first RNA molecule that is complementary to either the first DNA molecule or to the second DNA molecule; and (d) utilizing the first RNA molecule as a template to enzymatically synthesize a third DNA molecule that is complementary to the first RNA molecule. The third DNA molecules can be linked to dye molecules by aminoallyl linkages.

Conditions for hybridizing processed DNA samples of the invention to immobilized nucleic acid molecules. Typically, hybridization conditions are no more than 25° C. to 30° C. (for example, 110° C.) below the melting temperature (Tm) of the native duplex; see generally, Sambrook et al. *Molecular Cloning: A Laboratory Manual,* 2nd ed., Cold Spring Harbor Press, 1987; Ausubel et al., *Current Protocols in Molecular Biology*, Greene Publishing, 1987).

Tm for nucleic acid molecules greater than about 100 bases can be calculated by the formula $Tm=81.5+0.41\%(G+C)-\log(Na+)$. For oligonucleotide molecules less than 100 bases in length, exemplary hybridization conditions are 5 to 10° C. below Tm.

Preparation of microarrays. Nucleic acid molecules, that are to be hybridized to a processed DNA sample in accordance with this aspect of the invention, can be immobilized by any art-recognized means. For example, nucleic acid molecules (such as DNA or RNA molecules) can be immobilized to nitrocellulose, or to a synthetic membrane capable of binding nucleic acid molecules, or to a nucleic acid microarray, such as a DNA microarray. A DNA microarray, or chip, is a microscopic array of DNA fragments, including synthetic oligonucleotides, disposed in a defined pattern on a solid support, wherein they are amenable to analysis by standard hybridization methods (see, Schena, *BioEssays* 18:427, 1996).

The DNA in a microarray may be derived, for example, from genomic or cDNA libraries, from fully sequenced clones, or from partially sequenced cDNAs known as expressed sequence tags (ESTs). Methods for obtaining such DNA molecules are generally known in the art (see, e.g., Ausubel et al., eds., 1994, *Current Protocols in Molecular Biology*, vol. 2, Current Protocols Publishing, New York). Again by way of example, oligonucleotides may be synthesized by conventional methods, such as the methods described herein.

Microarrays can be made in a number of ways, of which several are described below. However produced, microarrays share certain preferred characteristics: The arrays are reproducible, allowing multiple copies of a given array to be produced and easily compared with each other. Preferably the microarrays are small, usually smaller than 5 cm², and they are made from materials that are stable under nucleic acid hybridization conditions. A given binding site or unique set of binding sites in the microarray will specifically bind the product of a single gene in the cell (or a nucleic acid molecule that represents the product of a single gene, such as a cDNA molecule that is complementary to all, or to part, of an mRNA molecule). Although there may be more than one physical binding site (hereinafter "site") per specific gene product, for the sake of clarity the discussion below will assume that there is a single site.

In one embodiment, the microarray is an array of polynucleotide probes, the array comprising a support with at least one surface and at least 100 different polynucleotide probes, each different polynucleotide probe comprising a different nucleotide sequence and being attached to the surface of the support in a different location on the surface. For example, the nucleotide sequence of each of the different polynucleotide probes can be in the range of 40 to 80 nucleotides in length. For example, the nucleotide sequence of each of the different polynucleotide probes can be in the range of 50 to 70 nucleotides in length. For example, the nucleotide sequence of each of the different polynucleotide probes can be in the range of 50 to 60 nucleotides in length.

In specific embodiments, the array comprises polynucleotide probes of at least 2,000, 4,000, 10,000, 15,000, 20,000, 50,000, 80,000, or 100,000 different nucleotide sequences.

In another embodiment, the nucleotide sequence of each polynucleotide probe in the array is specific for a particular target polynucleotide sequence. In yet another embodiment, the target polynucleotide sequences comprise expressed polynucleotide sequences of a cell or organism.

In a specific embodiment, the cell or organism is a mammalian cell or organism. In another specific embodiment, the cell or organism is a human cell or organism.

In specific embodiments, the nucleotide sequences of the different polynucleotide probes of the array are specific for at least 50%, at least 75%, at least 80%, at least 85%, at least 90%, at least 95%, or at least 99% of the genes in the genome of the cell or organism. Most preferably, the nucleotide sequences of the different polynucleotide probes of the array are specific for all of the genes in the genome of the cell or organism.

In specific embodiments, the polynucleotide probes of the array hybridize specifically and distinguishably to at least 10,000, to at least 20,000, to at least 50,000, to at least 80,000, or to at least 100,000 different polynucleotide sequences.

In other specific embodiments, the polynucleotide probes of the array hybridize specifically and distinguishably to at least 90%, at least 95%, or at least 99% of the genes or gene transcripts of the genome of a cell or organism. Most preferably, the polynucleotide probes of the array hybridize specifically and distinguishably to the genes or gene transcripts of the entire genome of a cell or organism.

In specific embodiments, the array has at least 100, at least 250, at least 1,000, or at least 2,500 probes per 1 cm², preferably all or at least 25% or 50% of which are different from each other.

In another embodiment, the array is a positionally addressable array (in that the sequence of the polynucleotide probe at each position is known).

In another embodiment, the nucleotide sequence of each polynucleotide probe in the array is a DNA sequence. In another embodiment, the DNA sequence is a single-stranded DNA sequence. The DNA sequence may be, e.g., a cDNA sequence, or a synthetic sequence.

When a nucleic acid molecule that corresponds to an mRNA of a cell (such as a third DNA molecule produced in the practice of the methods of the invention for synthesizing a preparation of nucleic acid molecules) is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) DNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In some embodiments, third DNA molecule populations prepared from RNA from two different cells are hybridized to the binding sites of the microarray. In the case of drug responses one biological sample is exposed to a drug and another biological sample of the same type is not exposed to the drug. In the case of pathway responses, one cell is exposed to a pathway perturbation and another cell of the same type is not exposed to the pathway perturbation. The third DNA molecules derived from each of the two cell types are differently labeled so that they can be distinguished. In one embodiment, for example, third DNA molecules from a cell treated with a drug (or exposed to a pathway perturbation) is synthesized using a fluorescein-labeled NTP, and third DNA molecules from a second cell, not drug-exposed, is synthesized using a rhodamine-labeled NTP. When the two populations of third DNA molecules are mixed and hybridized to the microarray, the relative intensity of signal from each population of third DNA molecules is determined for each site on the array, and any relative difference in abundance of a particular mRNA detected.

In the example described above, the third DNA molecule population from the drug-treated (or pathway perturbed) cell will fluoresce green when the fluorophore is stimulated and the third DNA molecule population from the untreated cell will fluoresce red. As a result, when the drug treatment has no effect, either directly or indirectly, on the relative abundance of a particular mRNA in a cell, the mRNA will be equally prevalent in both cells and, upon synthesis of third DNA molecules in accordance with the present invention, red-labeled and green-labeled third DNA molecules will be equally prevalent. When hybridized to the microarray, the binding site(s) for that species of RNA will emit wavelengths characteristic of both fluorophores (and appear brown in combination). In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Schena et al., 1995, *Science* 270:467-470, which is incorporated by reference in its entirety for all purposes. An advantage of using third DNA molecules labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use third DNA molecules from a single cell, and compare, for example, the absolute amount of a particular mRNA in, e.g., a drug-treated or pathway-perturbed cell and an untreated cell.

Preparation of nucleic acid molecules for immobilization on microarrays. As noted above, the "binding site" to which a particular, cognate, nucleic acid molecule specifically hybridizes is usually a nucleic acid or nucleic acid analogue attached at that binding site. In one embodiment, the binding sites of the microarray are DNA polynucleotides corresponding to at least a portion of each gene in an organism's genome. These DNAs can be obtained by, for example, polymerase chain reaction (PCR) amplification of gene segments from genomic DNA, cDNA (e.g., by reverse transcription or RT-PCR), or cloned sequences. Nucleic acid amplification primers are chosen, based on the known sequence of the genes or cDNA, that result in amplification of unique fragments (i.e., fragments that do not share more than 10 bases of contiguous identical sequence with any other fragment on the microarray). Computer programs are useful in the design of primers with the required specificity and optimal amplification properties. See, e.g., Oligo version 5.0 (National Biosciences). In the case of binding sites corresponding to very long genes, it will sometimes be desirable to amplify segments near the 3' end of the gene so that when oligo-dT primed DNA probes are hybridized to the microarray, less-than-full length probes will bind efficiently. Typically each gene fragment on the microarray will be between about 50 bp and about 2000 bp, more typically between about 100 bp and about 1000 bp, and usually between about 300 bp and about 800 bp in length.

Nucleic acid amplification methods are well known and are described, for example, in Innis et al., eds., 1990, *PCR Protocols: A Guide to Methods and Applications*, Academic Press Inc., San Diego, Calif., which is incorporated by reference in its entirety for all purposes. It will be apparent that computer controlled robotic systems are useful for isolating and amplifying nucleic acids.

An alternative means for generating the nucleic acid for the microarray is by synthesis of synthetic polynucleotides or oligonucleotides, e.g., using N-phosphonate or phosphoramidite chemistries (e.g., Froehler et al., 1986, *Nucleic Acid Res* 14:5399-5407). Synthetic sequences are typically between about 15 and about 100 bases in length, such as between about 20 and about 50 bases.

In some embodiments, synthetic nucleic acids include nonnatural bases, e.g., inosine. Where the particular base in a given sequence is unknown or is polymorphic, a universal base, such as inosine or 5-nitroindole, may be substituted. Additionally, it is possible to vary the charge on the phosphate backbone of the oligonucleotide, for example, by thiolation or methylation, or even to use a peptide rather than a phosphate backbone. The making of such modifications is within the skill of one trained in the art.

As noted above, nucleic acid analogues may be used as binding sites for hybridization. An example of a suitable nucleic acid analogue is peptide nucleic acid (see, e.g., Egholm et al., 1993, *Nature* 365:566-568; see also U.S. Pat. No. 5,539,083).

In another embodiment, the binding (hybridization) sites are made from plasmid or phage clones of genes, cDNAs (e.g., expressed sequence tags), or inserts therefrom (Nguyen et al., 1995, *Genomics* 29:207-209). In yet another embodiment, the polynucleotide of the binding sites is RNA.

Attaching nucleic acids to the solid support. The nucleic acid or analogue are attached to a solid support, which may be made from glass, silicon, plastic (e.g., polypropylene, nylon, polyester), polyacrylamide, nitrocellulose, cellulose acetate or other materials. In general, non-porous supports, and glass in particular, are preferred. The solid support may also be treated in such a way as to enhance binding of oligonucleotides thereto, or to reduce non-specific binding of unwanted substances thereto. Preferably, the glass support is treated with polylysine or silane to facilitate attachment of oligonucleotides to the slide.

Methods of immobilizing DNA on the solid support may include direct touch, micropipetting (see, e.g., Yershov et al., *Proc. Natl. Acad. Sci. USA* 93(10):4913-4918, 1996), or the use of controlled electric fields to direct a given oligonucleotide to a specific spot in the array (see, e.g., U.S. Pat. No. 5,605,662). DNA is typically immobilized at a density of 100 to 10,000 oligonucleotides per $cm^2$ such as at a density of about 1000 oligonucleotides per $cm^2$.

A preferred method for attaching the nucleic acids to a surface is by printing on glass plates, as is described generally by Schena et al., 1995, Science 270:467-470. This method is especially useful for preparing microarrays of cDNA. (See also DeRisi et al., 1996, *Nature Genetics* 14:457-460; Shalon et al., 1996, *Genome Res.* 6:639-645; and Schena et al., *Proc. Natl. Acad. Sci. USA,* 93(20):10614-19, 1996.)

In an alternative to immobilizing pre-fabricated oligonucleotides onto a solid support, it is possible to synthesize oligonucleotides directly on the support (see, e.g., Maskos et al., *Nucl. Acids Res.* 21:2269-70, 1993; Fodor et al., *Science* 251:767-73, 1991; Lipshutz et al., 1999, *Nat. Genet.* 21(1 Suppl):20-4). Methods of synthesizing oligonucleotides directly on a solid support include photolithography (see Fodor et al., *Science* 251:767-73, 1991; McGall et al., *Proc. Natl. Acad. Sci.* (*USA*) 93:13555-60, 1996) and piezoelectric printing (Lipshutz et al., 1999, *Nat. Genet.* 21(1 Suppl):20-4).

In one embodiment, a high-density oligonucleotide array is employed. Techniques are known for producing arrays containing thousands of oligonucleotides complementary to defined sequences, at defined locations on a surface using photolithographic techniques for synthesis in situ (see, Fodor et al., 1991, *Science* 251:767-773; Pease et al., 1994, *Proc. Natl. Acad. Sci. USA* 91:5022-5026; Lockhart et al., 1996, *Nature Biotechnol.* 14:1675-80; U.S. Pat. No. 5,578,832; U.S. Pat. No. 5,556,752; and U.S. Pat. No. 5,510,270; each of which is incorporated by reference in its entirety for all purposes) or other methods for rapid synthesis and deposition of defined oligonucleotides (Lipshutz et al., 1999, *Nat. Genet.* 21(1 Suppl):20-4.).

In one embodiment, microarrays are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioeletronics* 11:687-690; Blanchard, 1998, in *Synthetic DNA Arrays in Genetic Engineering*, Vol. 20, J. K. Setlow, Ed., Plenum Press, New York at pages 111-123; U.S. Pat. No. 6,028,189 to Blanchard. Specifically, the oligonucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes).

Other methods for making microarrays, e.g., by masking (Maskos and Southern, 1992, *Nuc. Acids Res.* 20:1679-1684), may also be used. In principal, any type of array, for example, dot blots on a nylon hybridization membrane (see Sambrook et al., 1989, *Molecular Cloning—A Laboratory Manual (2nd*

*Ed.*), Vols. 1-3, Cold Spring Harbor Laboratory, Cold Spring Harbor, N.Y.), could be used, although, as will be recognized by those of skill in the art, very small arrays will be preferred because hybridization volumes will be smaller.

Signal detection and data analysis. When fluorescently labeled probes are used, the fluorescence emissions at each site of a transcript array can be detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Research* 6:639-645, which is incorporated by reference in its entirety for all purposes). One embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Shalon et al., 1996, *Genome Res.* 6:639-645 and in other references cited herein. Alternatively, the fiber-optic bundle described by Ferguson et al., 1996, *Nature Biotechnol.* 14:1681-1684, may be used to monitor mRNA abundance levels at a large number of sites simultaneously.

Signals are recorded and, in one embodiment, analyzed by computer, e.g., using a 12 bit analog to digital board. In one embodiment the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

The relative abundance of an mRNA in two biological samples is scored as a perturbation and its magnitude determined (i.e., the abundance is different in the two sources of mRNA tested), or as not perturbed (i.e., the relative abundance is the same). In various embodiments, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation.

Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

By way of example, two samples, each labeled with a different fluor, are hybridized simultaneously to permit differential expression measurements. If neither sample hybridizes to a given spot in the array, no fluorescence will be seen. If only one hybridizes to a given spot, the color of the resulting fluorescence will correspond to that of the fluor used to label the hybridizing sample (for example, green if the sample was labeled with Cy3, or red, if the sample was labeled with Cy5). If both samples hybridize to the same spot, an intermediate color is produced (for example, yellow if the samples were labeled with fluorescein and rhodamine). Then, applying methods of pattern recognition and data analysis known in the art, it is possible to quantify differences in gene expression between the samples. Methods of pattern recognition and data analysis are described in e.g., International Publication WO 00/24936, dated May 4, 2000, which is incorporated by reference herein.

The following examples merely illustrate the best mode now contemplated for practicing the invention, but should not be construed to limit the invention.

EXAMPLE 1 cDNA Synthesis and RNA Amplification for the Preparation of Cy3— and Cy5-Labeled RNA Targets for Gene Expression Monitoring This Example describes the synthesis of a population of third DNA molecules prepared in accordance with the methods of the invention.

Isolation of total RNA. Total RNA was isolated from Jurkat and K562 cell lines by gentle lysis with the RNeasy Purification Kit (QIAGEN Inc., Valencia, Calif.).

Isolation of messenger RNA. Poly $A^+$ RNA was isolated from the total RNA to provide the template mRNA used in the experiment. Poly $A^+$ RNA was isolated by two sequential chromatographic purifications over oligo dT cellulose (New England Biolabs, Beverly, Mass.) using established protocols as described by Ausubel, F. M. et al. in *Current Protocols in Molecular Biology* 13.12.1-13.12.5 (eds. Ausubel, F. M. et al.) (John Wiley & Sons, New York, 1993). 1.5 µg of cytoplasmic mRNA was used in the subsequent procedure.

Synthesis of first DNA molecules. The following reverse transcription reaction was performed. The first primer mixture, called ShDNP256, included a multiplicit of primer molecules that each had the following nucleic acid sequence:

ShDNP256 5' TAG ATG CTG TTG NNN NNN NNN 3' (SEQ ID NO:3), wherein N represents any nucleic acid residue (e.g., A, C, G, T or I).

For each sample of template mRNA, the mRNA sample and the first primer mixture were added to an eppendorf tube in the following amounts:

mRNA (1.5 µg) 13.4 µl (adjust volume with water)
100 µM ShDNP256 (SEQ ID NO:3)1.6 µl
15.0 µl The preparation was incubated for 10 minutes (min) at 70° C., then for 5 min on ice, and then for 10 min at room temperature. The following reagents were prepared as a premix, and a 25µl aliquot was added to each sample (containing mRNA and first primer mixture) and mixed well:

| | |
|---|---|
| 10 mM dNTPs | 2.0 µl |
| 5X RT buffer | 8.0 µl |
| 50 mM MgCl$_2$ | 4.0 µl |
| 100 mM DTT | 4.0 µl |
| water | 6.0 µl |
| Superscript II (200 U/µl) | 1.0 µl |
| | 25.0 µl |

The reverse transcriptase utilized to synthesize the first DNA molecules was SUPERSCRIPT II RNase H—Reverse Transcriptase (item no. 18064-014, Gibco-BRL, Rockville, Md.). The composition of 5×RT buffer (supplied with the SUPERSCRIPT II enzyme) was 250 mM Tris-HCl (pH 8.3), 375 mM KCl, 15 mM MgCl$_2$ (Gibco-BRL, Rockville, Md.). The water added to the first DNA molecule synthesis mixture was DNase/RNase-free water (item no. 10977-015, Gibco-BRL, Rockville, Md.). Samples were incubated for 20 min at 42° C.

Alkaline hydrolysis of template RNA and purification of first DNA molecules. 20 µl of NaOH/EDTA (1:1 mix of 1 N NaOH and 0.5 M EDTA) was then added to each sample containing the products of the foregoing reverse transcription reaction. Samples were incubated for 20 min at 65° C. 20 µl of 1 M Tris-HCl, pH 7.6 was added and mixed. 20 µl of water was added.

The first DNA molecules in the treated samples were purified with QIAquick spin columns. 50 µl of Buffer PB (5:1 buffer to reaction volume) was added to each sample and mixed. Buffer PB was supplied with the QIAquick PCR Purification Kit (item no. 28106, QIAGEN Inc., Valencia, Calif.). Each sample was then applied to a column, spun for 1 min at top speed in a microcentrifuge, re-applied to the column and spun again. The flow-through from the column was discarded. The sample was then washed with 500 µl of Buffer PE, spun in the microcentrifuge, and the flow-through discarded. This wash was then repeated a second time. The sample was spun for an additional 1 min to remove residual PE. Buffer PE was supplied with the QIAquick PCR Purification Kit (item no. 28106, QIAGEN Inc., Valencia, Calif.).

The bound sample was eluted from the column by adding 50 µl of Buffer EB (10 mM Tris-HCl, pH 8.5), and incubating at room temp for 1 minute before spinning. The elution step was repeated, then the entire 100 µl eluate was quantitated in a 96-well UV Plate (Costar item no. 3635, Corning Inc., Corning, N.Y.) with the SPECTRAmax PLUS 384 Microplate Reader (item no. 0200-3855, Molecular Devices Corp., Sunnyvale, Calif.). The procedure typically yielded 450-600 ng of first DNA molecules per reverse transcription reaction. Each sample was concentrated to 18 µl with a Microcon-30 (Millipore) or speed-vac apparatus.

Synthesis of second DNA molecules. the first DNA molecules were used as templates to synthesize complementary second DNA molecules as follows. Second DNA molecule synthesis was primed using a second primer mixture called ShT7N9. Each primer of the second primer mixture had the following nucleic acid sequence:

ShT7N9 5' ACTA TAG GGA GAN NNN NNN NN 3' (SEQ ID NO:2)

Each second DNA molecule synthesis reaction included the following components mixed in an eppendorf tube:

| First DNA molecules | 18.0 µl |
|---|---|
| 100 µM ShT7N9(SEQ ID NO: 2) | 2.0 µl |
| | 20.0 µl |

Each reaction mixture was incubated for 5 min at 70° C., then incubated for 10 min at room temperature. The following reagents were then added to each reaction mixture and mixed well:

| RNase free water | 21.5 µl |
|---|---|
| React 2 buffer | 5.0 µl |

| -continued | |
|---|---|
| 10 M dNTPs | 2.5 µl |
| Klenow (5 U/µl) | 1.0 µl |
| | 30.0 µl |

The water added to the second DNA molecule synthesis mixture was DNase/RNase-free water (item no. 10977-015, Gibco-BRL, Rockville, Md.). The Klenow fragment of DNA Polymerase I was obtained from Gibco-BRL, Rockville, Md. (item no. 18012-039). The composition of 10× React 2 Buffer was 500 mM Tris-HCl (pH 8.0), 100 mM MgCl$_2$, 500 mM NaCl (Gibco-BRL, Rockville, Md.). Each reaction mixture was incubated for 1 hour at 37° C., then incubated for 2 min at 65° C.

Purification of double-stranded DNA molecules. The double-stranded DNA reaction products were purified with QIAquick spin columns (QIAGEN, Inc., Valencia, Calif.). 50 µl of water was added to each reaction mixture and the QIAquick spin column purification steps carried out as described above for the purification of the first DNA molecules.

Amplification of double-stranded DNA molecules. Using spectrophotometric quantitation of cDNA, 150 ng of each second strand synthesis product was added to a PCR tube and adjusted to 25 µl with DNase/RNase-free water. A pre-mix of the following reagents was made, and for each double-stranded DNA sample, 75 µl of the pre-mix was aliquoted into a PCR tube and mixed well. The T7 and DP256 primers had the following sequences:

```
                                    (SEQ ID NO:5)
T7      5' AAT TAA TAC GAC TCA CTA TAG GGA GA 3'

(SEQ ID NO:6)
DP256   5' GTT CGA GAC CTC TAG ATG CTG TTG 3'
```

| RNase free water | 48.0 µl |
|---|---|
| 10x PCR buffer | 10.0 µl |
| 50 mM MgCl$_2$ | 3.0 µl |
| 1 mM dNTPs | 10.0 µl |
| 100 µM T7 primer (SEQ ID NO: 5) | 1.0 µl |
| 100 µM DP256 primer(SEQ ID NO: 6) | 1.0 µl |
| Taq polymerase (5 U/µl) | 2.0 µl |
| | 75.0 µl |

The water added to the amplification mixture was DNase/RNase-free water (item no. 10977-015, Gibco-BRL, Rockville, Md.). The composition of 10×PCR Buffer was 200 mM Tris-HCl (pH 8.4), 500 mM KCl (Gibco-BRL, Rockville, Md.). The 1 mM dNTPs were diluted from a 10 mM dNTP mix purchased from Gibco-BRL, Rockville, Md. (item no. 18427-013). The T7 primer and DP256 primer were purchased from New England Biolabs, Beverly, Mass. The Taq DNA Polymerase was purchased from Gibco-BRL, Rockville, Md. (item no. 18038-042). The thermal cycler was started in advance and sample tubes were added when the temperature reached 94° C. The PCR reaction was run under the following cycle:

| | |
|---|---|
| 1 cycle of: | 94° C. for 5 min |
| 2 cycles of: | 94° C. for 45 sec |
| | 40° C. for 2 min |
| | 72° C. for 4 min |
| 8 cycles of: | 94° C. for 45 sec |
| | 55° C. for 2 min |
| | 72° C. for 4 min |

The reaction product was purified with a QIAquick spin column as described above for the purification of the first DNA molecules. All the PCR reactions derived from the same mRNA template sample were pooled. 100 µl of eluate was quantitated in a 96-well UV Plate as described above. The typical yield was 1.2-1.8 µg of double-stranded DNA per PCR reaction.

Synthesis of the first RNA molecules. For each sample, 500 ng of PCR product was aliquoted into an eppendorf tube and the volume was adjusted to 40 µl with DNase/RNase-free water. A pre-mix of the following reagents was made, and 40 µl was aliquoted into each sample and mixed well:

| | |
|---|---|
| water | 4.8 µl |
| 5X Transcription buffer | 16.00 µl |
| 100 mM DTT | 6.00 µl |
| 25 mM NTPs | 8.00 µl |
| 200 mM MgCl$_2$ | 3.30 µl |
| RNAGuard (36 U/µl) | 0.50 µl |
| Inorganic Pyrophosphate (2000 U/ml) | 0.6 µl |
| T7 RNA Polymerase (2.5 kU/µl) | 0.8 µl |
| | 40.00 µl |

The water added to the RNA synthesis mixture was DNase/RNase-free water (item no. 10977-015, Gibco-BRL, Rockville, Md.). The composition of 5× Transcription Buffer was 200 mM Tris-HCl (pH 7.5), 50 mM NaCl, 30 mM MgCl$_2$, 10 mM spermidine (item no. BP1001, EPICENTRE Technologies, Madison, Wis.). The 25 mM NTP's were diluted from a 100 mM NTP Set (item no. 27-2025-01, Pharmacia Biotech, Piscataway, N.J.). RNAguard Ribonuclease Inhibitor was purchased from Pharmacia Biotech, Piscataway, N.J. (item no. 27-0815-01). Inorganic Pyrophosphatase was purchased from New England Biolabs, Beverly, Mass. (item no. M0296S). The samples were incubated for 16 hours at 42° C. The samples were then incubated for 5 min at 70° C.

Purification of the first RNA molecules. The samples were purified with the RNeasy Purification Kit (QIAGEN Inc., Valencia, Calif.) as follows:
1. Add 20 µl of RNase-free water to the reaction mixture.
2. Add 350 µl of RLT Buffer and mix. The RLT Buffer was supplied with the RNeasy Purification Kit.
3. Add 250 µl of EtOH and mix.
4. Apply to spin column and spin for 20 sec at 14,000 rpm.
5. Reload sample onto same spin column, spin and discard flow-through.
6. Apply 500 µl of 80% EtOH, spin and discard flow-through.
7. Repeat wash step.
8. After discarding the flow-through, spin for 1 min to remove residual EtOH.
9. Elute by adding 50 µl of 70° C. water and incubate for 1 min at room temperature before spinning.
10. Repeat the elution step.

5 µl of eluate was added to 95 µl of TE (10 mM Tris-HCl, pH 7.3, 0.1 mM EDTA) and quantitated in a 96-well UV Plate as described above. The typical yield was 85-100 µg of first RNA molecules per RNA polymerase reaction.

Synthesis of third DNA molecules. First RNA molecules were used as templates for the synthesis of complementary third DNA molecules. The starting material [for one sample] was 3.0 µg of first RNA molecules purified from the preceding RNA polymerase reaction. For each sample, the following reagents were added to an eppendorf tube (the volume of RNA was adjusted in Dnase/Rnase-free water):

| | |
|---|---|
| RNA (3.0 µg) | 11.0 µl |
| N9 primer (SEQ ID NO: 7) (1 µg/µl) | 4.0 µl |
| | 15.0 µl |

The mixture was incubated for 10 min at 70° C., for 5 min on ice, then for 10 min at room temperature. A pre-mix of the following reagents was made and a 35 µl aliquot was added to each sample (containing N9 primer (SEQ ID NO:7) hybridized to first RNA molecules) and mixed well:

| | |
|---|---|
| 10 mM dNTPs | 2.5 µl |
| 10 mM aa-dUTP | 2.5 µl |
| 5X RT buffer | 10.0 µl |
| 50 mM MgCl$_2$ | 5.0 µl |
| 100 mM DTT | 5.0 µl |
| DNase/RNase-free water | 7.5 µl |
| Superscript II (200 U/µl) | 2.5 µl |
| | 35.0 µl |

10 mM aa-dUTP was purchased from Sigma, St. Louis, Mo. (item no. A 0410). The composition of 5×RT buffer was 250 mM Tris-HCl (pH 8.3), 375 mM KCl, 15 mM MgCl$_2$ (Gibco-BRL, Rockville, Md.). The samples were incubated at 42° C. for 20 min.

Alkaline hydrolysis of first RNA molecules and purification of third DNA molecules. 25 µl of NaOH/EDTA (1:1 mix of 1N NaOH and 0.5M EDTA) was then added. The samples were incubated at 65° C. for 20 min, then 25 µl of 1M Tris-HCl, pH 7.6 was added and mixed. Each sample was purified with a QIAquick (QIAGEN) spin column as follows:
1. Add 500 µl of Buffer PB (5:1 buffer to reaction volume) and mix.
2. Apply to column.
3. Spin for 1 min. at top speed in a microfuge.
4. Re-apply and spin again.
5. Discard flow-through.
6. Wash with 500 µl of Buffer PE, spin and discard flow-through.
7. Repeat wash one time.
8. Spin for an additional 1 min. to remove residual PE
9. Elute by adding 50 µl of Buffer EB (10 mM Tris-HCl, pH 8.5) and incubating at room temp for 1 min. before spinning
10. Repeat elution step The entire 100 µl eluate from each sample was quantitated in a 96-well plate. The typical yield was 1.5-2.1 µg of third DNA molecules per reverse transcription reaction. Optionally, each sample can be concentrated to approximately 10 µl in a Microcon-30 (Millipore). Each sample was dried down in a speed-vac and resuspended in 3.5 µl of water.

Labelling the third DNA molecules with Cy dye. Each cDNA sample was resuspended in 8 µl of 1× bicarbonate buffer (item no. C-3041, Sigma, St. Louis, Mo.). Lyophilized Cy3-NHS-ester (item no. Q13108, Pharmacia Biotech, Piscataway, N.J.) and Cy5-NHS-ester dyes (item no. Q13108, Pharmacia Biotech, Piscataway, N.J.) were resuspended in 367 and 400 µl of dimethyl sulfoxide (item no. D-8779, Sigma, St. Louis, Mo.), respectively. Then 8 µl of Cy3 or Cy5 dye was added to each sample and mixed thoroughly. Samples were then incubated at room temperature for 1 hour in the dark. Reactions were stopped by adding 8 µl of 4M hydroxylamine (item no. H-2391, Sigma, St. Louis, Mo.) followed by a 10 minute incubation in the dark at room temperature. Unincorporated dye molecules were removed with the QIAquick PCR Purification Kit (item no. 28106, QIAGEN Inc., Valencia, Calif.) as described earlier. The percent dye incorporation and cDNA yield were determined spectrophotometrically. Pairs of Cy3/Cy5-labelled cDNA samples were combined and hybridized to DNA microarrays.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of synthesizing a preparation of nucleic acid molecules, the method comprising the steps of:
   (a) utilizing an RNA template to enzymatically synthesize a population of first DNA molecules that are complementary to at least 50 contiguous bases of said RNA template, wherein the synthesis of the population of first DNA molecules is primed using a first primer mixture comprising a multiplicity of first primers, wherein each of the first primers comprises a random sequence portion, and a defined sequence portion;
   (b) utilizing the population of first DNA molecules as a template to enzymatically synthesize a population of second DNA molecules, thereby forming a population of double-stranded DNA molecules wherein the population of first DNA molecules is hybridized to the population of second DNA molecules;
   (c) utilizing the population of first or second DNA molecules of the double-stranded DNA molecules as a template to enzymatically synthesize a population of first RNA molecules that are complementary to either the first DNA molecules or to the second DNA molecules;
   (d) utilizing the population of first RNA molecules as a template to enzymatically synthesize a population of third DNA molecules that are complementary to the first RNA molecules; and
   (e) labeling the population of third DNA molecules with at least one dye molecule.

2. The method of claim 1 wherein the population of double-stranded DNA molecules is enzymatically amplified before utilizing the population of first or second DNA molecules of the double-stranded DNA molecules as a template to enzymatically synthesize a population of first RNA molecules.

3. The method of claim 2, wherein the RNA template is messenger RNA.

4. The method of claim 2, wherein the population of first DNA molecules is synthesized using reverse transcriptase.

5. The method of claim 1, wherein the defined sequence portion of each of said first primers is located 5' to the random sequence portion.

6. The method of claim 5, wherein the defined sequence portion comprises the nucleic acid sequence of an RNA polymerase promoter.

7. The method of claim 6, wherein the defined sequence portion comprises the nucleic acid sequence set forth in SEQ ID NO:1.

8. The method of claim 5, wherein each of the first primers consists of the nucleic acid sequence of primer ShT7N9 set forth in SEQ ID NO:2.

9. The method of claim 1, wherein the random sequence portion of said first primers consists of from 4 to 20 nucleic acid residues.

10. The method of claim 1, wherein the random sequence portion of each of said first primers consists of from 4 to 15 nucleic acid residues.

11. The method of claim 1, wherein the random sequence portion of said first primers consists of from 6 to 9 nucleic acid residues.

12. The method of claim 1, wherein the random sequence portion of each of said first primers consists of 9 nucleic acid residues.

13. The method of claim 1, wherein each of the first primers consists of the nucleic acid sequence of primer ShDNP256 set forth in SEQ ID NO:3.

14. The method of claim 1, wherein the first primer mixture further comprises a multiplicity of poly-dT primers, comprising a poly-dT portion and a defined sequence portion, wherein the poly-dT portion is located 5' to the defined sequence portion.

15. The method of claim 14, wherein the sequence of the defined sequence portion of the poly-dT primer is identical to the sequence of the defined sequence portion of the primers of the first primer mixture.

16. The method of claim 14, wherein the poly-dT portion of the poly-dT primer consists of from 5 to 25 nucleic acid residues.

17. The method of claim 14, wherein the poly-dT portion of the poly-dT primer consists of from 15 to 25 nucleic acid residues.

18. The method of claim 14, wherein the poly-dT portion of the poly-dT primer consists of 18 nucleic acid residues.

19. The method of claim 1, further comprising the step of hydrolyzing the RNA template, and substantially removing the first primer mixture, after synthesizing the population of first DNA molecules and before synthesizing the population of second DNA molecules.

20. The method of claim 2, wherein the population of second DNA molecules is synthesized using the Klenow fragment of DNA polymerase I.

21. The method of claim 1, wherein the synthesis of the population of second DNA molecules is primed using a second primer mixture comprising a multiplicity of second primer molecules, wherein each second primer molecule comprises a random sequence portion and a defined sequence portion, wherein the sequence of the defined sequence portion of the second primer molecules is different from the sequence of the defined sequence portion of the first primer molecules.

22. The method of claim 21, wherein the defined sequence portion of the second primer molecules is located 5' to the random sequence portion of the second primer molecules.

23. The method of claim 21, wherein the defined sequence portion of each second primer molecule comprises the nucleic acid sequence of an RNA polymerase promoter.

24. The method of claim 23 wherein the defined sequence portion of each first primer molecule does not comprise the nucleic acid sequence of an RNA polymerase promoter.

25. The method of claim 23, wherein the defined sequence portion of each second primer molecule comprises the nucleic acid sequence set forth in SEQ ID NO. 1.

26. The method of claim 23, wherein each second primer molecule consists of the nucleic acid sequence of primer ShT7N9 set forth in SEQ ID NO. 2.

27. The method of claim 21 wherein the defined sequence portion of each first primer molecule comprises the nucleic acid sequence of an RNA polymerase promoter, and the defined sequence portion of each second primer molecule does not comprise the nucleic acid sequence of an RNA polymerase promoter.

28. The method of claim 21 wherein the second primer molecule consists of the nucleic acid sequence of primer ShDNP256, set forth in SEQ ID NO:3.

29. The method of claim 21 wherein each first primer consists of the nucleic acid sequence of primer ShDNP256 set forth in SEQ ID NO:3, and each second primer consists of the nucleic acid sequence of primer ShT7N9, set forth in SEQ ID NO:2.

30. The method of claim 2, wherein the population of double-stranded DNA molecules is amplified using a polymerase chain reaction comprising from 1 to 25 amplification cycles.

31. The method of claim 30, wherein the number of amplification cycles is from 5 to 15.

32. The method of claim 30, wherein the number of amplification cycles is 10.

33. The method of claim 2, further comprising the step of purifying the amplified, double-stranded, DNA molecules before synthesizing the population of first RNA molecules.

34. The method of claim 2, wherein the population of first DNA molecules of the amplified, double-stranded, DNA molecules is utilized as a template to enzymatically synthesize the population of first RNA molecules.

35. The method of claim 34, wherein the population of first DNA molecules of the amplified, double-stranded, DNA molecules comprises a T7 RNA polymerase promoter that promotes synthesis of the population of first RNA molecules.

36. The method of claim 35, wherein the T7 RNA polymerase promoter comprises the nucleic acid sequence set forth in SEQ ID NO. 1.

37. The method of claim 35, wherein the T7 RNA polymerase promoter consists of the nucleic acid sequence set forth in SEQ ID NO. 1.

38. The method of claim 2, wherein the population of second DNA molecules of the amplified, double-stranded, DNA molecules is utilized as a template to synthesize the population of first RNA molecules.

39. The method of claim 38, wherein the population of second DNA molecules comprises a T7 RNA polymerase promoter which promotes the synthesis of the population of first RNA molecules.

40. The method of claim 39, wherein the T7 RNA polymerase promoter comprises the nucleic acid sequence set forth in SEQ ID NO. 1.

41. The method of claim 39, wherein the T7 RNA polymerase promoter consists of the nucleic acid sequence set forth in SEQ ID NO. 1.

42. The method of claim 2, further comprising the step of purifying the population of first RNA molecules before synthesizing the population of third DNA molecules, wherein the purification step removes substantially all nucleic acid molecules less than 100 bases long.

43. The method of claim 2, wherein the population of third DNA molecules is synthesized using reverse transcriptase, and the synthesis of the population of third DNA molecules is primed using a population of random primers.

44. The method of claim 43 wherein at least 99 percent of the random primers consist of nine nucleotides.

45. The method of claim 2, wherein the population of third DNA molecules is purified to remove substantially all nucleic acid molecules less than 100 bases long.

46. The method of claim 1, wherein the at least one dye molecule is joined to the third DNA molecules by aminoallyl linkages.

47. The method of claim 46 wherein the dye is a Cy dye.

48. A method of synthesizing a preparation of nucleic acid molecules, the method comprising the steps of:
   (a) utilizing an RNA template to enzymatically synthesize a population of first DNA molecules that are complementary to at least 50 contiguous bases of the RNA template, wherein:
      (i) the population of first DNA molecules is synthesized using reverse transcriptase;
      (ii) the synthesis of the population of first DNA molecules is primed using a first primer mixture comprising a multiplicity of first primers, wherein each of the first primers comprises a random sequence portion and a defined sequence portion located 5' to the random sequence portion, wherein the defined sequence portion comprises a nucleic acid sequence selected from the group consisting of SEQ ID NO:2 and SEQ ID NO:3;
(b) hydrolyzing the template RNA and removing substantially all of the first primer mixture after synthesis of the population of first DNA molecules;
(c) utilizing the population of first DNA molecules as a template to enzymatically synthesize a population of second DNA molecules, thereby forming a population of double-stranded DNA molecules wherein the population of first DNA molecules is hybridized to the population of second DNA molecules, wherein:
 (i) the population of second DNA molecules is synthesized using the Klenow fragment of DNA polymerase I;
 (ii) the synthesis of the population of second DNA molecules is primed using a second primer mixture comprising a multiplicity of second primer molecules, wherein each second primer molecule comprises a random sequence portion and a defined sequence portion, wherein the sequence of the defined sequence portion of each second primer molecule is different from the sequence of the defined sequence portion of each first primer molecule, and wherein the second primer defined sequence portion comprises a nucleic acid sequence selected from the group consisting of SEQ ID NO:2 and SEQ ID NO:3;
(d) removing substantially all of the second primer mixture after synthesis of the population of second DNA molecules;
(e) amplifying the population of double-stranded DNA molecules using a polymerase chain reaction comprising from 5 to 15 amplification cycles, wherein the polymerase chain reaction is primed with a first PCR primer population and a second PCR primer population, wherein the first PCR primer population consists essentially of primer molecules consisting of the sequence set forth in SEQ ID NO:5, and the second PCR primer population consists essentially of primer molecules consisting of the sequence set forth in SEQ ID NO:6;
(f) removing substantially all of the PCR primer mixture after amplification of the population of double-stranded DNA molecules;
(g) utilizing the population of first or second DNA molecules of the amplified, double-stranded, DNA molecules as a template to synthesize, using an RNA polymerase, a population of first RNA molecules that are complementary to either the first DNA molecules or to the second DNA molecules;
(h) purifying the population of first RNA molecules to remove substantially all nucleic acid molecules less than 100 bases long;
(i) utilizing the population of first RNA molecules as a template to enzymatically synthesize a population of third DNA molecules that are complementary to the first RNA molecules, wherein the population of third DNA molecules is synthesized using reverse transcriptase and the synthesis of the population of third DNA molecules is primed using a population of random primers wherein substantially all of the random primers consist of 9 bases; and
(j) joining Cy dye molecules to the third DNA molecules by aminoallyl linkages.

49. A method of synthesizing a preparation of nucleic acid molecules, the method comprising the steps of:
(a) utilizing an RNA template to enzymatically synthesize a population of first DNA molecules that are complementary to at least 50 contiguous bases of said RNA template;
(b) utilizing the population of first DNA molecules as a template to enzymatically synthesize a population of second DNA molecules, thereby forming a population of double-stranded DNA molecules wherein the population of first DNA molecules is hybridized to the population of second DNA molecules;
(c) enzymatically amplifying the double-stranded DNA molecules;
(d) utilizing the population of first or second DNA molecules of the amplified double-stranded DNA molecules as a template to enzymatically synthesize a population of first RNA molecules that are complementary to either the first DNA molecules or to the second DNA molecules; and
(e) utilizing the population of first RNA molecules as a template to enzymatically synthesize a population of third DNA molecules that are complementary to the first RNA molecules.

50. The method of claim 49, wherein the synthesis of the population of first DNA molecules is primed using a first primer mixture comprising a multiplicity of first primers, wherein each of the first primers comprises a random sequence portion, and a defined sequence portion located 5' to the random sequence portion.

* * * * *

UNITED STATES PATENT AND TRADEMARK OFFICE
CERTIFICATE OF CORRECTION

PATENT NO. : 7,432,084 B2  Page 1 of 1
APPLICATION NO. : 10/485008
DATED : October 7, 2008
INVENTOR(S) : D. D. Shoemaker et al.

It is certified that error appears in the above-identified patent and that said Letters Patent is hereby corrected as shown below:

| COLUMN | LINE | ERROR |
|---|---|---|
| Title Page item (54) Pg. 1, col. 1 | Title | "METHODS FOR PREPARING NUCLEIC ACID SAMPLES" should read --METHODS FOR PREPARING NUCLEIC ACID SAMPLES USEFUL FOR SCREENING DNA ARRAYS-- |
| 1 | 1-2 | "METHODS FOR PREPARING NUCLEIC ACID SAMPLES" should read --METHODS FOR PREPARING NUCLEIC ACID SAMPLES USEFUL FOR SCREENING DNA ARRAYS-- |

Signed and Sealed this

Twenty-third Day of June, 2009

JOHN DOLL
*Acting Director of the United States Patent and Trademark Office*